United States Patent
Ueno et al.

(10) Patent No.: US 7,022,732 B2
(45) Date of Patent: Apr. 4, 2006

(54) PROPANOLAMINE DERIVATIVE HAVING 1, 4-BENZODIOXANE RING

(75) Inventors: Masahiro Ueno, Ohimachi (JP); Koji Kawamura, Ohimachi (JP); Makoto Yanai, Ohimachi (JP); Toshihiro Takahashi, Ohimachi (JP); Nobuhiro Kinoshita, Ohimachi (JP); Koichi Katsuyama, Ohimachi (JP); Satoko Fuchizawa, Ohimachi (JP); Shigeru Hiramoto, Ohimachi (JP)

(73) Assignees: Nisshin Pharma Inc., Tokyo (JP); Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/489,332

(22) PCT Filed: Sep. 13, 2001

(86) PCT No.: PCT/JP01/07951

§ 371 (c)(1),
(2), (4) Date: Apr. 21, 2004

(87) PCT Pub. No.: WO03/024953

PCT Pub. Date: Mar. 27, 2003

(65) Prior Publication Data

US 2004/0235921 A1 Nov. 25, 2004

(51) Int. Cl.
*A61K 31/36* (2006.01)
*C07D 319/20* (2006.01)

(52) U.S. Cl. ........................ 514/452; 549/362
(58) Field of Classification Search ............... 549/362; 546/282.4; 548/454; 514/452, 338, 414
See application file for complete search history.

(56) References Cited

U.S. PATENT DOCUMENTS 4,338,333 A   7/1982   Ainsworth et al.

FOREIGN PATENT DOCUMENTS

| EP | 0 455 006 | 11/1991 |
| FR | 2746395 | 9/1997 |
| JP | 11-140079 | 5/1999 |
| WO | 94/18161 | 8/1994 |
| WO | 96/35685 | 11/1996 |

OTHER PUBLICATIONS

Joseph M. Ready et al., "Asymmetric Catalytic Synthesis of α-Aryloxy Alcohols: Kinetic Resolution of Terminal Epoxides via Highly Enantioselective Ring-Opening with Phenols", J. Am. Chem. Soc., 121, 6086-6087, 1999.

W. J. Rzeszotarski et al., "Cardioselectivity of β-adrenoceptor blocking agents. 2. Role of the amino group substituent", Journal of Medical Chemistry, (1983), vol. 26, No. 5, pp. 644-648; especially, table II.

*Primary Examiner*—Bernard Dentz
(74) *Attorney, Agent, or Firm*—Wenderoth, Lind & Ponack, L.L.P.

(57) ABSTRACT

This invention relates to a medicament containing as an active ingredient, a novel propanolamine having a 1,4-benzodioxane ring or a pharmaceutically acceptable salt thereof:

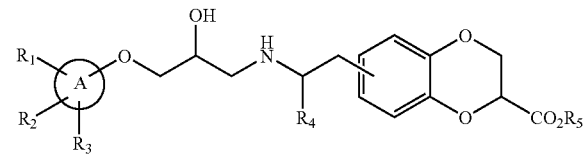

(I)

The present compound is represented by the above formula wherein $R_{1-3}$ may be the same or different and each represents a hydrogen atom, a halogen atom, a hydroxy group, a ($C_1$–$C_6$)alkyl group, a ($C_1$–$C_6$)alkoxy group, a ($C_1$–$C_6$) alkylsulfonamido group, or a phenyl group; $R_{4-5}$ each represents a hydrogen atom or a ($C_1$–$C_6$)alkyl group; and A represents any of a benzene ring, a pyridine ring and a pyrimidine ring.

This compound is useful as a prophylactic or therapeutic agent for diabetes, obesity, hyperlipemia, depression, a respiratory disease, or a gastrointestinal disease.

6 Claims, No Drawings

PROPANOLAMINE DERIVATIVE HAVING 1,4-BENZODIOXANE RING

This application is a 371 of PCT/JP01/07951 filed Sep. 13, 2001.

TECHNICAL FIELD

This invention relates to novel propanolamine derivatives having a 1,4-benzodioxane ring and medicaments containing them as active ingredients. The derivatives are useful as prophylactic or therapeutic agents for diabetes, obesity or hyperlipemia. They are also useful as prophylactic or therapeutic agents for depression, a respiratory disease, a gastrointestinal disease (including peptic ulcer, esophagitis, duodenitis, acute or chronic gastritis (including cases induced by *H. pyroli*), Crohn's disease, ulcerative colitis, an irritable bowel syndrome involving cholecystitis, biliary dyskinesia, or abdominal pain, nausea, vomiting, epigastrium discomfort, etc.) in a mammal.

BACKGROUND ART

Diabetes is a disease which fails to sufficiently utilize glucose in the body. It follows that an increase in blood glucose level or chronic hyperglycemia is caused and various complications are induced. It is important to normalize blood glucose level in the treatment of diabetes. For that purpose, parenteral administration of insulin (an in vivo hormone which regulates blood glucose), oral administration of drugs and dietary therapy have now been carried out. Diabetes is classified into two major forms of type I diabetes and type II diabetes. Type I diabetes is the result of a deficiency of insulin, which is basically improved by administration of insulin. On the other hand, type II diabetes, which is insulin-nondependent diabetes, occurs in the face of normal or even elevated levels of insulin. This means that the tissue response to insulin is not normal. In the treatment of type II diabetes, oral administration of drugs which promote insulin secretion or repress absorption of sugar contained in the diet, parenteral administration of insulin and dietary therapy have been carried out. However, these are not fundamental methods for the treatment of diabetes, and patients frequently suffer from side effects and pains. Therefore, it has been earnestly desired to develop newer drugs that improve the pathosis of diabetes. In addition, a majority of cases of the type II diabetes are known to be associated with obesity, which suggests that the crisis of diabetes is closely related to the obesity. It is also known that, in a patient suffering from diabetes and obesity, diabetes is improved by eliminating obesity. Obesity is thought to be caused by accumulation of fat in the body, and in order to improve obesity, it is necessary to consume the accumulated fat. Recently, obesity or diabetes has become a problem in not only humans but also in pets due to excess nutrition and lack of exercise. Additionally, a method for decreasing fat and increasing lean meat has been desired for edible animals.

It is known that β-adrenergic receptors are divided into β1-, β2- and β3-subtypes. Stimulation of β1 receptor mainly causes an increase in heart rate. Stimulation of β2 receptor mainly causes bronchodilation and smooth muscle relaxation. Stimulation of β3 receptor mainly promotes lipolysis and energy consumption, by which a decrease in fat mass results. Accordingly, it is thought that compounds having β3 agonistic activity possess ant-obesity activity. In addition, it is reported that these compounds have anti-hyperglycemic activity in animal models of type II diabetes. These indicate that β3 agonists are useful in improving obesity in mammals and hyperglycemia in diabetes of mammals. The leading β3 agonists known at the present time include those described below, for example.

As one of the compounds, Ainsworth et al. disclose in Japanese Patent Kokai 56-5444 (JP 56-5444A) a compound (BRL 37344) of the following formula (III), its carboxylic acid methyl ester (BRL 35135) and their pharmaceutically acceptable salts.

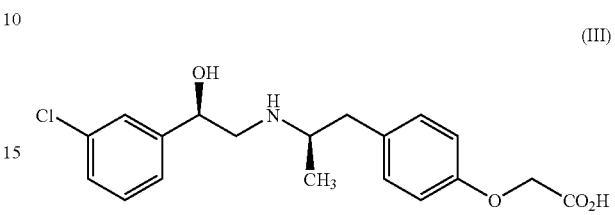

(III)

These compounds have anti-obesity activity and anti-hyperglycemic activity. However, it is reported that side-effects, namely tremor caused by stimulation of β2 receptors, have been observed in clinical trials.

Bloom et al., in Japanese Patent Kokai 5-320153 (JP 05-320153A), disclose a compound of the following formula (IV) and a pharmaceutically acceptable salt thereof.

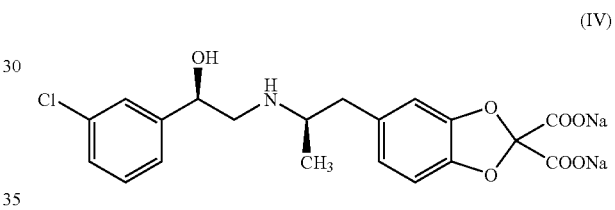

(IV)

This compound has potent activity to β3 receptor in rodents and further has very high selectivity to β1 and β2 receptors. However, its efficacy in clinical trials has not been observed because of its weak activity to human β3 receptor.

Takahashi et al., in WO 96/35685, disclose a compound of the following formula (V) and a pharmaceutically acceptable salt thereof.

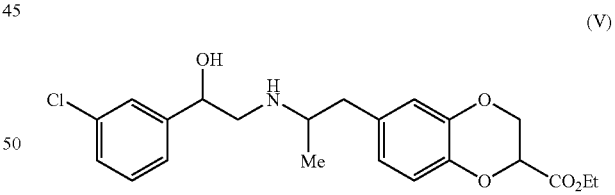

(V)

Guillaumet et al., in FR 2746395, disclose a compound of the following formula (VI) and its pharmaceutically acceptable salt thereof.

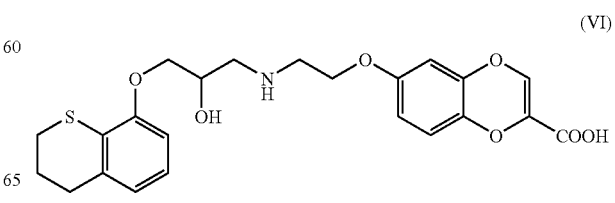

(VI)

Although the activity to human β3 receptor is described in these cases, whether or not the compounds may have sufficiently useful activity and high selectivity is not indicated. Moreover, they do not mention the fact that the level of intrinsic activity is critical.

β3 Agonists are useful as anti-obesity agents or anti-hypoglycemic agents. However, the existing β3 agonists have disadvantages such that side effects will develop because they possess activity to β1 and β2 receptors, etc. other than β3 receptor or their activity to human β3 adrenergic receptor is weak despite of the activity to animal β3 receptor. In addition, one of the reasons that sufficient efficacy cannot be expected is believed to be that they are not full agonists but partial agonists, even if they have activity to human β3 receptor.

Under these circumstances, it has been desired to develop compounds having high activity and selectivity to human β3 receptor as well as having high intrinsic activity.

DISCLOSURE OF THE INVENTION

The present inventors made intensive studies with the aim at compounds which have high activity and selectivity to human β3 adrenergic receptor as well as have high intrinsic activity. As a result, the inventors have found that propanolamine derivatives having specific structures possess significant agonistic activity to human β3 adrenergic receptor and high intrinsic activity, on which this invention has been completed.

Specifically, this invention relates to a propanolamine derivative having a 1,4-benzodioxane ring represented by the general formula (I):

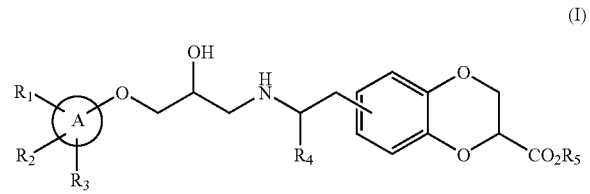

(I)

wherein $R_1$, $R_2$ and $R_3$ may be the same of different, and each represents a hydrogen atom, a halogen atom, a $(C_1-C_6)$alkyl group, a $(C_1-C_6)$alkoxy group, a $(C_1-C_6)$alkoxy$(C_1-C_6)$alkoxy group, a phenyl group, a naphthyl group, a phenoxy group, a naphthyloxy group, a phenyl$(C_1-C_6)$alkyloxy group, a $(C_1-C_6)$alkylsulfonyloxy group, a hydroxy group, a $(C_1-C_6)$alkylsulfonamido group, an amino group, a mono- or di-$(C_1-C_6)$alkylamino group, a carboxy group, a carboxamido group, a $(C_1-C_6)$-alkoxycarbonyl group, a mercapto group, a formyl group, a cyano group, a tetrazolyl group, or a nitro group; or $R_1$ and $R_2$ together may form a saturated or unsaturated 5-membered or 6-membered ring wherein the 5-membered or 6-membered ring may contain several S, N or O atoms; and the alkylene chain in $R_1$, $R_2$ and $R_3$ may be substituted with 1–3 halogen atoms, hydroxy groups or amino groups, $R_4$ represents a hydrogen atom or a $(C_1-C_6)$alkyl group, $R_5$ represents a hydrogen atom or a $(C_1-C_6)$alkyl group, and A represents any of a benzene ring, a pyridine ring and a pyrimidine ring, or a pharmacologically acceptable salt thereof.

This invention also relates to a prophylactic or therapeutic agent for diabetes, obesity or hyperglycemia in a mammal which comprises a compound of the general formula (I) or a pharmacologically acceptable salt thereof as an active ingredient. This invention further relates to a prophylactic or therapeutic agent for depression, a respiratory disease, or a gastrointestinal disease (including peptic ulcer, esophagitis, duodenitis, acute or chronic gastritis (including cases induced by H. pyroli), Crohn's disease, ulcerative colitis, an irritable bowel syndrome involving cholecystitis, biliary dyskinesia, abdominal pain, nausea, vomiting, epigastrium discomfort, etc.) in a mammal, the agent comprising a compound of the general formula (I) or a pharmacologically acceptable salt thereof as an active ingredient.

In the general formula (I) of this invention, the halogen atom represented by $R_1$, $R_2$ or $R_3$ includes fluorine, chlorine, bromine and iodine. The $(C_1-C_6)$alkoxy group includes a straight or branched alkoxy, such as methoxy, ethoxy, propoxy, isopropoxy, butoxy, isobutoxy, t-butoxy, pentyloxy, isopentyloxy, hexyloxy and isohexyloxy group, etc. The $(C_1-C_6)$alkoxy$(C_1-C_6)$alkoxy group includes a methoxymethoxy, methoxyethoxy, ethoxymethoxy, ethoxyethoxy group, etc. The phenyl$(C_1-C_6)$alkyloxy group includes a phenylmethoxy, phenylethoxy, phenylpropoxy, phenylbutoxy, phenylpentoxy, phenylhexyl group, etc. The $(C_1-C_6)$alkylsulfonyloxy group includes a methanesulfonyloxy, ethanesulfonyloxy group, etc. The $(C_1-C_6)$alkylsulfonamido group includes a methanesulfonamido, ethanesulfonamido group, etc. The mono- or di-$(C_1-C_6)$alkylamino group includes a methylamino, dimethylamino, ethylamino, diethylamino group, etc. The $(C_1-C_6)$alkoxycarbonyl group includes a methoxycarbonyl ethoxycarbonyl group, etc. The $(C_1-C_6)$alkyl group represented by $R_1$, $R_2$, $R_3$, $R_4$ or $R_5$ includes straight or branched alkyl, such as methyl, ethyl, propyl, isopropyl, butyl, sec-butyl, t-butyl, pentyl, isopentyl, hexyl, isohexyl groups, etc. The 5-membered ring which $R_1$ and $R_2$ together form includes a pyrrole ring, a furan ring, a thiophene ring, pyrazole ring, an imidazole ring, a thiazole ring, an isoxazole ring, an oxazole ring, etc.; and the 6-membered ring includes a pyridine ring, a pyrazine ring, a pyrimidine ring, a pyridazine ring, etc.

In this invention, propanolamine derivatives having a 1,4-benzodioxane ring represented by the general formula (II):

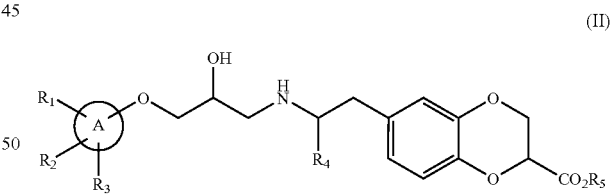

(II)

(wherein $R_1$, $R_2$, $R_3$, $R_4$, $R_5$ and A are as defined above) are particularly useful.

The preferred compounds of this invention are the compounds of the above formula (I) or (II) wherein $R_1$, $R_2$ and $R_3$ may be the same or different and each represents a hydrogen atom, a halogen atom, a $(C_1-C_6)$alkoxy group, a $(C_1-C_6)$alkoxy$(C_1-C_6)$alkoxy group, a hydroxy group, a $(C_1-C_6)$alkylsulfonamido group, or an amino group; or $R_1$ and $R_2$ together may form a benzene ring, a pyrrole ring, a furan ring, a thiophene ring, a pyrazole ring, an imidazole ring, a thiazole ring, an isoxazole ring, an oxazole ring or —OCH$_2$O—; $R_4$ represents a hydrogen atom or a $(C_1-C_6)$ alkyl group; $R_5$ represents a hydrogen atom or a $(C_1-C_6)$ alkyl group; and A represent any of a benzene ring, a pyridine ring and a pyrimidine ring, or pharmacologically acceptable salts thereof.

The more preferred compounds of this invention are the compounds of the above formula (I) or (II) wherein $R_1$, $R_2$ and $R_3$ may be the same or different and each represents a hydrogen atom, a halogen atom, a $(C_1-C_6)$alkoxy group, a $(C_1-C_6)$alkoxy$(C_1-C_6)$alkoxy group, a hydroxy group, a $(C_1-C_6)$alkylsulfonamido group, or an amino group; or $R_1$ and $R_2$ together may form a benzene ring, a pyrrole ring, a furan ring, an imidazole ring or $-OCH_2O-$; $R_4$ represents a hydrogen atom or a $(C_1-C_6)$alkyl group; $R_5$ represents a hydrogen atom or a $(C_1-C_6)$alkyl group; and A represents any of a benzene ring, a pyridine ring and a pyrimidine ring, or pharmacologically acceptable salts thereof.

The still more preferred compounds of this invention are the compounds of the above formula (I) or (II) wherein $R_1$, $R_2$ and $R_3$ may be the same or different and each represents a hydrogen atom, a methoxy group, a methoxymethoxy group, a hydroxy group, a methanesulfonamido group, or an amino group; or $R_1$ and $R_2$ together may form a pyrrole ring; $R_4$ represents a hydrogen atom or a methyl group; $R_5$ represents a hydrogen atom, a methyl group or an ethyl group; and A represents either of a benzene ring and a pyridine ring, or pharmacologically acceptable salts thereof.

The compounds of this invention include possible optical isomers, metabolites and metabolite precursors for the compounds of the general formula (I). The metabolites include those wherein A and the benzodioxane are hydroxylated, or the hydroxy group is further sulfated or glucuronide-conjugated. The compounds of the general formula (I) according to this invention may be prepared by various conventional processes, for example, the process as shown below.

A propanolamine derivative having a 1,4-benzodixane ring represented by the general formula (X):

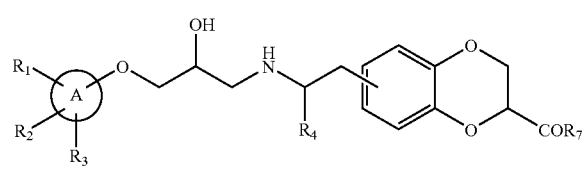
(X)

is prepared by reacting a compound of the general formula (VII):

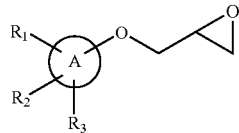
(VII)

(wherein $R_1$, $R_2$ and $R_3$ are as defined in the general formula (I)) with a compound of the general formula (VIII):

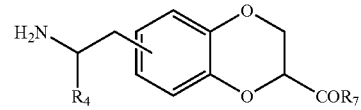
(VIII)

(wherein $R_4$ is as defined in the general formula (I) and $R_7$ is a $(C_1-C_6)$alkoxy group or a group of the general formula (IX):

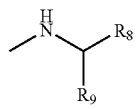
(IX)

(wherein $R_8$ and $R_9$ are a methyl group or a phenyl group, provided that when the one is a methyl group, the other is a phenyl group)) (Step A). The compound of the general formula (X) may be converted to, if necessary, a compound of the general formula (XI) in a free acid form:

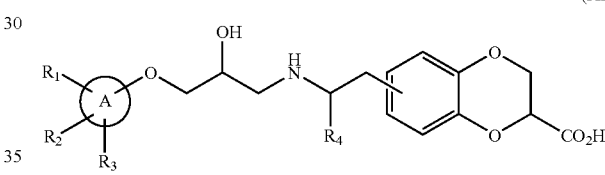
(XI)

by neutralization or hydrolysis (Step B).

Step A is carried out in the presence of a base. The bases to be used include hydroxides such as sodium hydroxide, potassium hydroxide, calcium hydroxide, lithium hydroxide, barium hydroxide, and magnesium hydroxide; carbonates such as sodium carbonate, potassium carbonate, silver carbonate, and sodium hydrogencarbonate; organic amines such as triethylamine, tri-n-butylamine, diisopropylethylamine, diethylamine, and diisopropylamine; and pyridines such as pyridine and 4-dimethylaminopyridine.

Reaction may optionally be carried out in the presence of a silylation agent such as trimethylsilylacetamide or chlorotrimethylsilane.

Additives may optionally be added to reaction. Additives include phase transfer catalysts such as tetramethylammonium chloride, tetramethylammonium bromide, tetramethylammonium iodide, tetramethylammonium hydroxide, tetraethylammonium chloride, tetraethylammonium bromide, tetraethylammonium iodide, tetraethylammonium hydroxide, tetrapropylammonium chloride, tetrapropylammonium bromide, tetrapropylammonium iodide, tetrapropylammonium hydroxide, tetrabutylammonium chloride, tetrabutylammonium bromide, tetrabutylammonium iodide, tetrabutylammonium hydroxide, tetrapentylammonium chloride, tetrapentyloammonium bromide, tetrapentylammonium iodide, tetrapentylammonium hydroxide, tetrahexylammonium chloride, tetrahexyloammonium bromide, tetrahexylammonium iodide, tetrahexylammonium hydroxide, tetraheptylammonium chloride, tetraheptylammonium bromide, tetraheptylammonium iodide, tetraheptylammonium hydroxide, tetraoctylammonium chloride, tetraoctylammonium bromide, tetraoctylammonium iodide, and tetraoctylammonium hydroxide.

Reaction may be carried out by a process wherein a compound (VIII) is used at 1 molar equivalent to 10 molar equivalents to a compound (VII) and all of the compound (VIII) is added at the beginning of the reaction or the compound (VIII) is added to the compound (VII) in small portions at predetermined intervals.

The solvents to be used are not particularly limited insofar as they do not adversely affect the reaction.

There are preferably used, for example, hydrocarbons such as benzene, toluene, xylene, hexane, and heptane; halogenated hydrocarbons such as chloroform, methylene chloride, 1,2-dichloroethane, and carbon tetrachloride; ethers such as diethyl ether, diisopropyl ether, diphenyl ether, tetrahydrofuran, and 1,4-dioxane; amides such as dimethylformamide, dimethylacetamide, and hexamethylphosphoric triamide; alcohols such as methanol, ethanol, 1-propanol, 2-propanol, 1-butanol, and tert-butanol; sulfoxides such as dimethyl sulfoxide; organic acids such as acetic acid and propionic acid; ketones such as acetone and 2-butanone; esters such as ethyl acetate and butyl acetate; organic amines such as triethylamine, diisopropylethylamine, and pyridine; acetonitrile; water; and a mixture of the foregoing.

Reaction is carried out under ice-cooling to under heating at reflux. Reaction time varies depending on reagents, reaction temperature, chemical equivalents, etc., but it is usually from 0.5 to 72 hours. Preferably, reaction is carried out under heating at reflux a compound (VII) and one molar equivalent to 3 molar chemical equivalents of a compound (VIII) in an ethanol solvent for 24 to 48 hours.

The compound of the general formula (VII) in the above preparation process (Step A) is available as a commercial product or may be prepared, for example, by the process described below.

Specifically, it is prepared by reacting a compound of the general formula (XII):

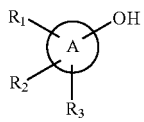

(XII)

(wherein $R_1$, $R_2$ and $R_3$ are as defined in the general formula (I)) with a compound of the general formula (XIII):

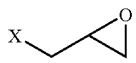

(XIII)

(wherein X is a halogen atom or a sulfonate).

This step is carried out in the presence or absence of an inorganic base (such as sodium carbonate, potassium carbonate, or sodium hydrogencarbonate), a tertiary amine (such as triethylamine or diisopropylamine), or a pyridine (such as pyridine or 4-dimethylaminopyridine).

The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water or a mixed solvent of the foregoing, as previously described.

Reaction is carried out under ice-cooling to under heating at reflux. Reaction time varies depending on reagents, reaction temperature, chemical equivalents, etc., but it is usually from 0.5 to 24 hours. Preferably, reaction is carried out in a solvent of dimethyformamide or acetone in the presence of potassium carbonate at from 20 to 100° C. for 6 to 20 hours.

The halogen atom for X includes chlorine, bromine and iodine; the sulfonate group includes a mesyloxy group, a tosyloxy group, an m-nitrosulfonyloxy group, and the like.

Of the compound of the general formula (VII) in the above preparation process (Step A), an optically active compound is available as a commercial product or may be prepared by various conventional processes, for example, reaction of a compound of the general formula (XII) with an optically active compound of the general formula (XIII).

A compound of the general formula (VII) may be prepared by alkali treatment of a compound of the general formula (XV):

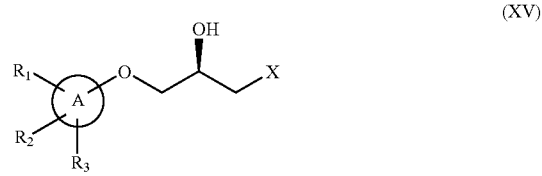

(XV)

(wherein X is a halogen atom or a sulfonate), which is obtained in the asymmetric reduction of a compound of the general formula (XIV):

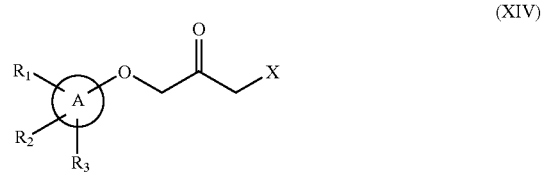

(XIV)

(wherein X is a halogen atom or a sulfonate).

Alternatively, it may be prepared according to the process described below. Specifically, it may be prepared by reacting a compound of the general formula (XII):

(XII)

(wherein $R_1$, $R_2$ and $R_3$ are as defined in the general formula (I)) with a compound of the general formula (XVII):

(XVII)

(wherein X' is a halogen atom) in the presence of a (salen) Co(III)complex (XVI), which is reported by N. Jacobsen et al., J. Am. Chem. Soc., 121, 6086–6087 (1999),

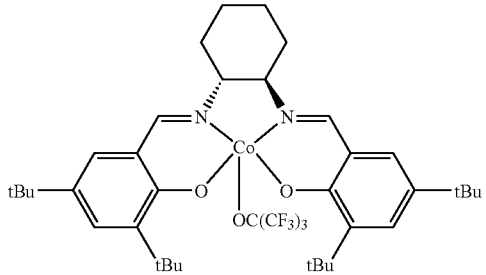

(XVI)

to obtain a compound of the general formula (XVIII):

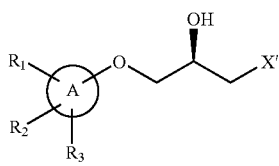

(XVIII)

(wherein X' is a halogen atom), which is then subjected to alkali treatment.

The compound of the general formula (VIII) in the above preparation process (Step A) may be prepared by various conventional processes, for example, the process as disclosed in Japanese Patent Kokai No. 140079/1999 (JP 11-140079A). When $R_4$ is a hydrogen atom, a compound of the general formula (XIX) obtained, for example, by the process disclosed in WO96/35865,

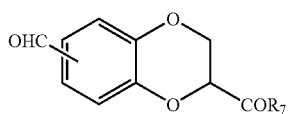

(XIX)

(wherein $R_7$ is as defined in the general formula (VIII)) is allowed to react with a compound of the general formula (XX):

$R_{10}NH_2$ (XX)

(wherein $R_{10}$ is $(C_1–C_6)$alkyl or $(C_3–C_8)$cycloalkyl) to prepare a compound of the general formula (XXI):

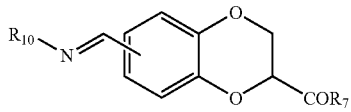

(XXI)

(wherein $R_7$ is as defined in the general formula (VIII) and $R_{10}$ is as defined in the general formula (XX)) (Step C), followed by reaction with nitromethane to prepare a compound of the general formula (XXII):

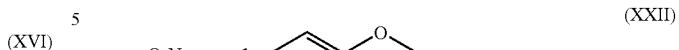

(XXII)

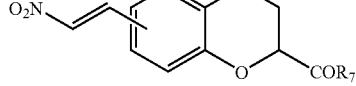

(wherein $R_7$ is as defined in the general formula (VIII)) (Step D), and then this compound is reduced to prepare a compound of the general formula (XXIII):

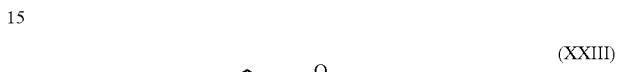

(XXIII)

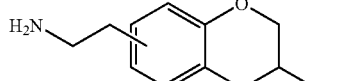

(wherein $R_7$ is as defined in the general formula (VIII)) (Step E).

Step C is a step to prepare a compound of the above general formula (XXI) and is usually carried out in the presence or absence of a solvent using a primary amine represented by the formula (XX). Reaction may be carried out while the water as produced is removed by means of a Dean-Stark trap or the like; or alternatively, it may be carried out in the presence of anhydrous sodium carbonate, anhydrous potassium carbonate, anhydrous sodium sulfate anhydrous calcium chloride, anhydrous magnesium sulfate or molecular sieve. Usually, reaction is preferably carried out in the presence of a solvent.

The amine represented by the general formula (XX) includes, for example, methylamine, ethylamine, butylamine, and cyclohexylamine. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described.

Reaction is carried out under ice-cooling to under heating at reflux. Reaction time varies depending on reagents, reaction temperature, etc., but it is usually from 0.5 to 12 hours. Preferably, reaction is carried out in a hydrocarbon solvent under heating at reflux for one to 5 hours. More preferably, reaction is carried out under heating at reflux in benzene or toluene for one to 3 hours to effect dehydration.

Step D is a step to prepare a compound of the general formula (XXII) and is usually carried out in the presence or absence of a solvent and in the presence of an acid. The acids to be used include inorganic acids such as hydrochloric acid, and sulfuric acid; organic acids such as acetic acid, propionic acid, and pivalic acid; and sulfonic acids such as methane sulfonic acid, toluene sulfonic acid, and camphorsulfonic acid.

The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described.

Reaction is carried out under ice-cooling to under heating at reflux. Reaction time varies depending on reaction temperature, etc., but it is usually from 3 to 12 hours. Preferably, reaction is carried out under heating at reflux in an organic acid, particularly acetic acid for one to 5 hours.

Step E is a step to prepare a compound of the above general formula (XXIII). Reduction of the nitro group or the olefin bond in Step E may be carried out using one or two sets of reaction conditions. For reduction, there may be used catalytic reduction or a reducing agent.

The reducing agents to be used include metal hydrides such as lithium borohydride, sodium borohydride, sodium borocyanohydride, lithium aluminum hydride, diisobutyla-luminum hydride, and sodium borotriacetoxyhydride.

Reaction is usually carried out in the presence of a solvent. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing. Reaction is carried out under ice-cooling to under heating at reflux. Reaction time varies depending on reagents, reaction temperature, chemical equivalents, etc., but it is usually from 0.5 to 24 hours. Preferably, reaction is carried out under ice-cooling to 50° C. in a solvent of alcohol in the presence of sodium borohydride, sodium borocyanohydride or sodium borotriacetoxyhydride for one to 5 hours.

When catalytic hydrogenation is carried out, reaction is carried out in the presence of a catalyst. With respect to the catalyst for use, there are preferably used a catalytic hydrogen catalyst such as palladium-carbon, platinum oxide, or palladium hydroxide. The solvents to be used are not particularly limited insofar as they do not adversely affect the reaction. There are preferably used, for example, the hydrocarbons, halogenated hydrocarbons, ethers, amides, alcohols, organic acids, esters, ketones or organic amines, acetonitrile, water, or a mixed solvent of the foregoing, as previously described. Hydrogen gas under atmospheric pressure, or hydrogen gas under medium or high pressure, preferably hydrogen gas with 1–5 kg/cm² is used for reaction. Reaction is carried out under ice-cooling to under heating at reflux. Reaction time varies depending on reagents, reaction temperature, chemical equivalents, etc., but it is usually from 0.5 to 24 hours. Preferably, reaction is carried out under hydrogen atmosphere at 0–80° C. in a solvent of alcohol using platinum oxide.

The hydrolysis or neutralization step of Step B is carried out in water or a mixed solvent of water/organic solvent in the presence of an acid. The acids to be used include, for example, inorganic acids such as hydrochloric acid, sulfuric acid, hydrobromic acid and nitric acid; organic acids such as acetic acid and propionic acid; and sulfonic acids such as methanesulfonic acid, p-toluenesiulfonic acid, and camphorsulfonic acid. The solvent to be used for reaction may be water alone or a mixed solvent of water and an organic solvent. Any organic solvents may be used insofar as they do not adversely affect the reaction. There are preferably used, for example, the hydrocarbons, halogenated hydrocarbons, ethers, amides, alcohols, organic acids, esters, ketones, acetonitrile, water, or a mixed solvent of the foregoing, as previously described. Reaction is carried out at from 20° C. to heating at reflux. Reaction time varies depending on the solvent, reagent and temperature to be used, but it is usually from one to 100 hours.

As an alternative process, a compound of the general formula (XXIV):

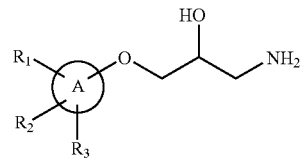

(XXIV)

(wherein $R_1$, $R_2$, $R_3$ and A are as defined in the general formula (I)) is allowed to react with a compound of the general formula (XXV):

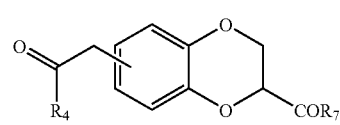

(XXV)

(wherein $R_4$ is as defined in the general formula (I) and $R_7$ is a $(C_1-C_6)$alkoxy group or a group of the general formula (IX):

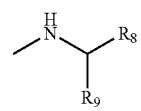

(IX)

(wherein $R_8$ and $R_9$ are a methyl group or a phenyl group, provided that when the one is a methyl group, the other is a phenyl group)) in a solvent to prepare a compound of the general formula (XXVI):

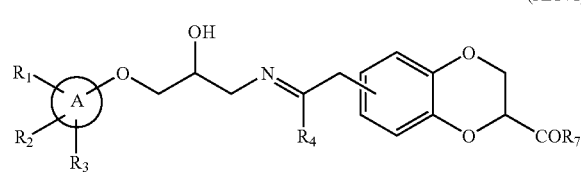

(XXVI)

(wherein $R_1$, $R_2$, $R_3$, $R_4$ and A are as defined in the general formula (I) and $R_7$ is as defined above) (Step F), and this compound is reduced to prepare a propanolamine derivative having a 1,4-benzodioxane ring represented by the general formula (X):

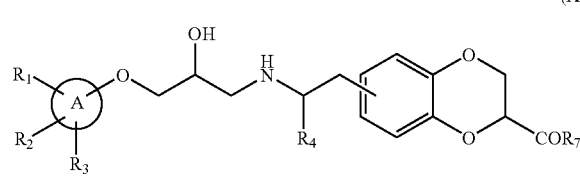

(X)

(Step G) and this compound is, if necessary, neutralized or hydrolyzed to prepare a compound of the general formula (XI):

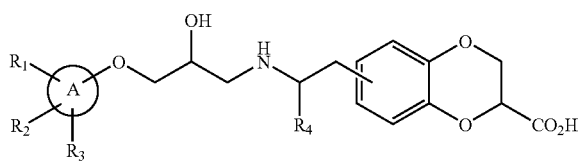

(Step B).

Step F is a step to prepare a compound of the above general formula (XXVI) and is usually carried out in the presence of a solvent. Reaction may be carried out while the water as produced is removed by means of a Dean-Stark trap or the like; or alternatively, it may be carried out in the presence of a dehydrating agent such as anhydrous sodium carbonate, anhydrous potassium carbonate, anhydrous sodium sulfate anhydrous calcium chloride, anhydrous magnesium sulfate or molecular sieve.

The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile or a mixed solvent of the foregoing, as previously described. Reaction is carried out under ice-cooling to under heating at reflux. Reaction time varies depending on reagents, reaction temperature, chemical equivalents, etc., but it is usually from 0.5 to 12 hours. Preferably, reaction is carried out under heating at reflux in a solvent of hydrocarbon or alcohol for one to 5 hours to effect dehydration. More preferably, reaction is carried out by heating at reflux in benzene or toluene for one to 3 hours to effect dehydration.

Step G is a step to prepare a compound of the above general formula (X). It is usually carried out by hydrogenation in the presence of a reducing agent or a catalyst. With respect to the reducing agents for use, there are, for example, preferably used metal hydrides such as lithium borohydride, sodium borohydride, sodium cyanoborohydride, lithium aluminum hydride, diisobutylaluminum hydride, and sodium triacetoxyborohydride.

Reaction is usually carried out in the presence of a solvent. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described. Reaction is carried out under ice-cooling to heating at reflux. Reaction time varies depending on reagents, reaction temperature, chemical equivalents, etc., but it is usually from 0.5 to 24 hours. Preferably, reaction is carried out under ice-cooling to 50° C. in a solvent of alcohol in the presence of sodium borohydride, sodium cyanoborohydride or sodium triacetoxyborohydride for one to 5 hours.

When catalytic hydrogenation is carried out, reaction is carried out in the presence of a catalyst. With respect to the catalysts for use, there are preferably used catalytic hydrogen catalysts such as palladium-carbon, and platinum oxide, palladium hydroxide. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described. Hydrogen gas under atmospheric pressure, or hydrogen gas under medium or high pressure, preferably hydrogen gas with 1–5 kg/cm$^2$ is used for reaction. Reaction is carried out under ice-cooling to under heating at reflux. Reaction time varies depending on reagents, reaction temperature, chemical equivalents, etc., but it is usually from 0.5 to 24 hours. Preferably, reaction is carried out under hydrogen atmosphere at 0–80° C. for 0.5 to 12 hours in a solvent of alcohol using platinum oxide.

The above Steps F and G may be optionally carried out in the same vessel. Specifically, a compound of the general formula (XXV) may be prepared from a compound of the general formula (XXIV) and a compound of the general formula (XXV) in a solvent under catalytic hydrogenation conditions or in the presence of a reducing agent. With respect to the catalysts for use, there are preferably used catalytic hydrogen catalysts such as palladium-carbon, platinum oxide, and palladium hydroxide. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described. Hydrogen gas under atmospheric pressure, or hydrogen gas under medium or high pressure, preferably hydrogen gas with 1–5 kg/cm$^2$ is used for reaction. Reaction is carried out under ice-cooling to under heating at reflux. Reaction time varies depending on reagents, reaction temperature, chemical equivalents, etc., but it is usually from 0.5 to 24 hours. Preferably, reaction is carried out under hydrogen atmosphere at 0–50° C. for 0.5 to 12 hours in a solvent of alcohol, more preferably in a solvent of alcohol in the presence of an organic acid such as acetic acid using platinum oxide as a catalyst.

In the process using a reducing agent, reaction is usually carried out in the presence of a solvent. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described. Reaction is carried out under ice-cooling to under heating at reflux. Reaction time varies depending on reagents, reaction temperature, chemical equivalents, etc., but it is usually from 0.5 to 24 hours. Preferably, reaction is carried out under ice-cooling to 50° C. for one to 5 hours in a solvent of alcohol in the presence of sodium borohydride, sodium cyanoborohydride, or sodium triacetoxyborohydride.

As an alternative process, a compound of the general formula (XXIV):

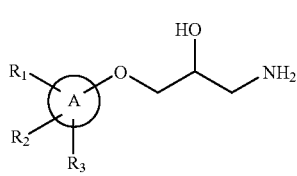

(wherein $R_1$, $R_2$, $R_3$ and A are as defined in the general formula (I)) is allowed to react with a compound of the general formula (XXVII):

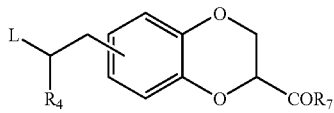

(XXVII)

(wherein L is a leaving group such as chloride, bromide, iodide, or sulfonate, $R_4$ is as defined in the general formula (I) and $R_7$ is a $(C_1-C_6)$alkoxy group or a group of the general formula (IX):

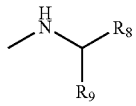

(IX)

(wherein $R_8$ and $R_9$ are a methyl group or a phenyl group, provided that when the one is a methyl group, the other is a phenyl group)) in a solvent to prepare a propanolamine derivative having a 1,4-benzodioxane ring of the general formula (X):

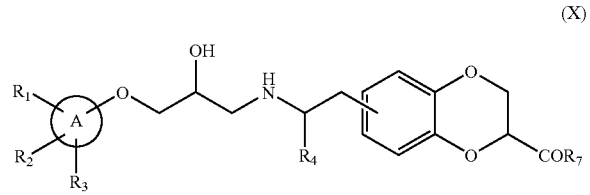

(X)

(Step H) and this compound is, if necessary, neutralized or hydrolyzed to prepare a compound of the general formula (XI):

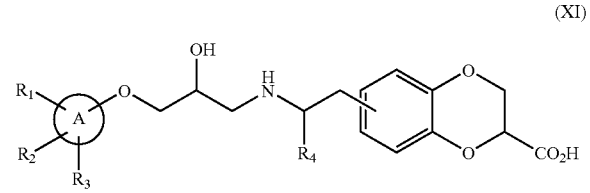

(XI)

(Step B).

Step H is carried out in the presence or absence of an inorganic base (such as sodium carbonate, potassium carbonate, or sodium hydrogencarbonate), a tertiary amine (such as triethylamine or diisopropylamine) or a pyridine (such as pyridine or 4-dimethylaminopyridine). Reaction is preferably carried out in the presence of a silylation agent such as trimethylsilylacetamide or chlorotriethylsilane. The solvents to be used are not particularly limited insofar as they do not adversely affect the reaction. There are preferably used, for example, the hydrocarbons, halogenated hydrocarbons, ethers, amides, alcohols, organic acids, esters, ketones, organic amines, acetonitrile, water, or a mixed solvent of the foregoing, as previously described. Reaction may be also carried out in the absence of a solvent.

Reaction is carried out under ice-cooling to under heating at reflux. Reaction time varies depending on reagents, reaction temperature, chemical equivalents, etc., but it is usually from 0.5 to 24 hours.

The compounds of the general formula (I) according to this invention may be, if desired, converted to addition salts with pharmacologically acceptable acids, and these acid addition salts are also included within the scope of this invention. The acid addition salts include, for example, salts with inorganic acids such as hydrochloric acid, sulfuric acid, and phosphoric acid, and salts with organic acids such as acetic acid, succinic acid, oxalic acid, malic acid, tartaric acid, malonic acid, fumaric acid, and maleic acid.

Of the compounds of the general formula (I) according to this invention, the compounds wherein $R_5$ is hydrogen may be, if desired, converted to addition salts with pharmacologically acceptable alkali metals, and these alkali metal addition salts are also included within the scope of this invention. The alkali metal addition salts include, for example, sodium salts, lithium salts, and potassium salts.

The compounds of the general formula (I) and salts thereof according to this invention have β3 agonistic activity, anti-hypoglycemic activity and anti-obesity activity. Accordingly, they are useful as prophylactic or therapeutic agents for diabetes, obesity or hyperlipemia in mammals including humans and pets. They are also useful as prophylactic and/or therapeutic agents for depression, a respiratory disease, or a gastrointestinal diseases (including peptic ulcer, esophagitis, duodenitis, acute or chronic gastritis (including cases induced by *H. pyroli*), Crohn's disease, ulcerative colitis, an irritable bowel syndrome involving cholecystitis, biliary dyskinesia, abdominal pain, nausea, vomiting, epigastrium discomfort, etc.), and further they are useful as a method for decreasing fat and increasing lean meat in edible animals.

This invention will then be more specifically explained by way of Examples, Preparation Examples, Pharmacological Examples with the present compounds and Pharmaceutical Preparation Examples, but this invention is not to be limited thereto. In Preparation Examples, there are illustrated specific examples for the preparation of intermediates to synthesize the compounds of this invention.

EXAMPLE 1

6-[2-(R)-[2-(S)-Hydroxy-3-[3-methanesulfonamido-4-(methoxymethoxy)phenoxy]propylamino]propyl]-2,3-dihydro-1,4-benzodioxine-2-(R)-carboxylic acid ethyl ester

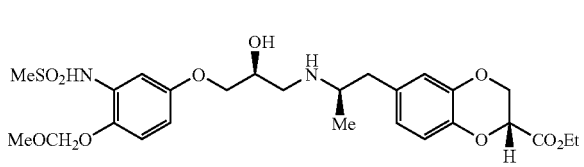

A solution of N-(2-methoxymethoxy-5-(S)-oxiranylmethoxyphenyl)methanesulfonamide (177 mg) obtained in Preparation Example 2 and 6-[2-(R)-aminopropyl-2,3-dihydro-1,4-benzodioxine-2-(R)-carboxylic acid ethyl ester (310 mg) in ethanol (5 mL) was stirred under reflux for 16 hours. After allowing to cool to room temperature, it was concentrated under reduced pressure. The residue was purified by column chromatography on silica gel and the title compound (200 mg) was obtained from the effluent with chloroform/methanol/aqueous ammonia=93/7/0.1 (v/v/v). Yield: 61%

$^1$H-NMR (CDCl$_3$) δ: 1.09 (d, 3H, J=6.4 Hz), 1.24–1.31 (m, 3H), 2.55 (dd, H, J=6.8 Hz, 13.6 Hz), 2.69 (dd, 1H, J=6.8 Hz, 13.6 Hz), 2.78 (dd, 1H, J=8.0 Hz, 12.4 Hz), 2.86–2.95 (m, 2H), 2.99 (s, 3H), 3.48 (s, 3H), 3.91 (d, H, J=5.2 Hz), 3.93–4.02 (m, 1H), 4.22–4.32 (m, 2H), 4.33–4.41 (m, 2H), 4.79 (dd, 1H, J=3.2 Hz, 4.4 Hz), 5.14 (s, 2H), 6.62 (dd, 1H, J=2.8 Hz, 8.8 Hz), 6.68–6.73 (m, 2H), 6.89–6.94 (m, 1H), 7.06 (d, 1H, J=8.8 Hz), 7.13–7.16 (m, 1H).

EXAMPLE 2

6-[2-(R)-[2-(S)-Hydroxy-3-(4-hydroxy-3-methanesulfonamidophenoxy)propylamino]propyl]-2,3-dihydro-1,4-benzodioxine-2-(R)-carboxylic acid

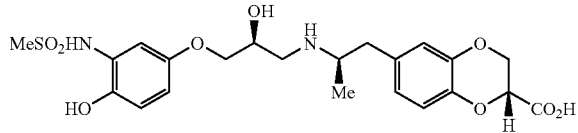

A solution of 6-[2-(R)-[2-(S)-hydroxy-3-[3-methanesulfonamido-4-(methoxymethoxy)phenoxy]propylamino]propyl]-2,3-dihydro-1,4-benzodioxine-2-(R)-carboxylic acid ethyl ester (220 mg) obtained in Example 1 in 1N—HCl (9 mL) was stirred under reflux for 3 hours. After allowing to cool to room temperature, it was concentrated to dryness under reduced pressure. The residue was dissolved in water/acetonitrile=1/1(v/v) (10 mL) and the pH was adjusted to 6.0 by addition of saturated aqueous sodium bicarbonate. After concentrating under reduced pressure, the residue was purified by HP column chromatography and the title compound was obtained from the effluent with water/methanol=50/50 (v/v). Yield: 62%

$^1$H-NMR (DMSO-d$_6$, 40° C.) δ: 1.03 (d, 3H, J=6.8 Hz), 2.30–2.41 (m, 1H), 2.81–3.04 (m, 2H), 2.95 (s, 3H), 3.07–3.14 (m, 2H), 3.78–3.92 (m, 2H), 4.15–4.29 (m, 2H), 4.33–4.42 (m, 1H), 4.65–4.76 (m, 1H), 6.55–6.69 (m, 3H), 6.77–6.89 (m, 3H).

EXAMPLE 3

6-[2-[2-(S)-Hydroxy-3-[3-methanesulfonamido-4-(methoxymethoxy)phenoxy]propylamino]ethyl]-2,3-dihydro-1,4-benzodioxine-2-(R)-carboxylic acid ethyl ester

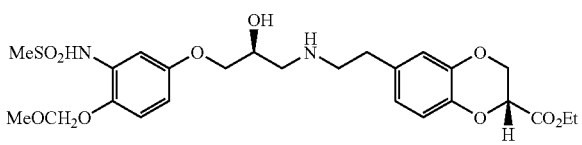

To a solution of 6-(2-nitroethyl)-2,3-dihydro-1,4-benzodioxine-2-(R)-carboxylic acid ethyl ester (910 mg) obtained in Preparation Example 4 in ethanol (35 mL) was added platinum oxide (91 mg) at room temperature. This solution was stirred under hydrogen atmosphere at room temperature for 8 hours and then filtered through Celite. The filtrate was concentrated to about half its volume under reduced pressure, and to this was added N-[2-methoxymethoxy-5-(S)-oxiranylmethoxyphenyl]methanesulfonamide obtained in Preparation Example 2 (335 mg) was added. This solution was stirred at room temperature for 16 hours and then under reflux for 5 hours. After allowing to cool to room temperature, it was concentrated under reduced pressure. The residue was purified by column chromatography on silica gel and the title compound (330 mg) was obtained from the effluent with chloroform/methanol/aqueous ammonia=93/7/0.1 (v/v). Yield: 54%

$^1$H-NMR (CDCl$_3$) δ: 1.29 (t, 3H, J=7.2 Hz), 2.68–2.79 (m, 3H), 2.82–2.94 (m, 3H), 2.99 (s, 3H), 3.48 (s, 3H), 3.87–3.96 (m, 2H), 3.97–4.04 (m, 1H), 4.22–4.32 (m, 2H), 4.34–4.39 (m, 2H), 4.79 (t, 1H, J=3.6 Hz), 5.14 (s, 2H), 6.62 (dd, 1H, J=3.2 Hz, 8.8 Hz), 6.70–6.76 (m, 2H), 6.90–6.95 (m, 1H), 7.06 (d, 1H, J=8.8 Hz), 7.15 (d, 1H, J=3.2 Hz).

EXAMPLE 4

6-[2-[2-(S)-Hydroxy-3-(4-hydroxy-3-methanesulfonamido-phenoxy]propylamino]ethyl]-2,3-dihydro-1,4-benzodioxine-2-(R)-carboxylic acid

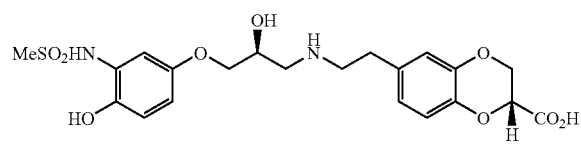

The title compound was prepared using 6-[2-[2-(S)-hydroxy-3-[3-methanesulfonamido-4-(methoxymethoxy)phenoxy]-propylamino]ethyl]-2,3-dihydro-1,4-benzodioxine-2-(R)-carboxylic acid ethyl ester obtained in Example 3 in the same manner as in Example 2. Yield: 88%

$^1$H-NMR (DMSO-d$_6$, 40° C.) δ: 2.52–2.66 (m, 2H), 2.78–2.95 (m, 3H), 2.93 (s, 3H), 2.98–3.06 (m, 1H), 3.77–3.86 (m, 2H), 4.04–4.13 (m, 1H), 4.16–4.24 (m, 1H), 4.30–4.37 (m, 1H), 4.44–4.51 (m, 1H), 6.50–6.64 (m, 3H), 6.70–6.84 (m, 3H).

EXAMPLE 5

6-[2-(R)-[2-(S)-Hydroxy-3-phenoxypropylamino]propyl-2,3-dihydro-1,4-benzodioxine-2-(R)-carboxylic acid ethyl ester

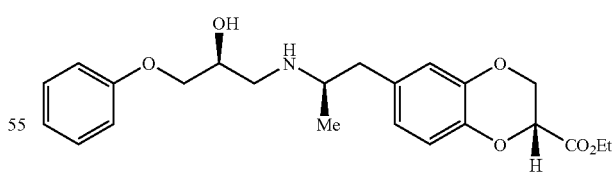

The title compound was prepared using 2-phenoxymethyl-(S)-oxirane in the same manner as in Example 1. Yield: 48%

$^1$H-NMR (CDCl$_3$) δ: 1.07 (d, 3H, J=5.6 Hz), 1.29 (t, 3H, J=7.2 Hz), 2.53 (dd, 1H, J=6.8 Hz, 13.6 Hz), 2.64 (dd, 1H, J=6.4 Hz, 13.6 Hz), 2.72–2.81 (m, 1H), 2.83–2.94 (m, 2H), 3.90–4.00 (m, 3H), 4.20–4.32 (m, 2H), 4.33–4.40 (m, 2H), 4.79 (dd, 1H, J=3.2 Hz, 4.0 Hz), 6.66–6.75 (m, 2H), 6.87–7.00 (m, 3H), 7.23–7.35 (m, 2H).

EXAMPLE 6

6-[2-(R)-[2-(S)-Hydroxy-3-phenoxypropylamino]propyl]-2,3-dihydro-1,4-benzodioxine-2-(R)-carboxylic acid

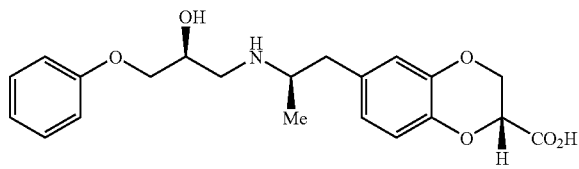

The title compound was prepared using 6-[2-(R)-[2-(S)-hydroxy-3-phenoxypropylamino]propyl]-2,3-dihydro-1,4-benzodioxine-2-(R)-carboxylic acid ethyl ester obtained in Example 5 in the same manner as in Example 2. Yield: 83%

$^1$H-NMR (DMSO-$d_6$, 40° C.) δ: 0.92 (d, 3H, J=5.2 Hz), 2.66 (dd, 1H, J=8.8 Hz, 13.2 Hz), 2.61 (dd, 1H, J=4.8 Hz, 13.2 Hz), 2.71–2.98 (m, 3H), 3.84–4.06 (m, 3H), 4.18 (dd, 1H, J=6.0 Hz, 10.8 Hz), 4.24–4.32 (m, 1H), 4.33–4.41 (m, 1H), 6.49–6.61 (m, 2H), 6.75 (d, 1H, J=8.0 Hz), 6.87–6.96 (m, 3H), 7.27 (t, 2H, J=8.0 Hz).

EXAMPLE 7

6-[2-(R)-[3-(2-Chlorophenoxy)-2-(S)-hydroxypropylamino]-propyl]-2,3-dihydro-1,4-benzodioxine-2-(R)-carboxylic acid ethyl ester

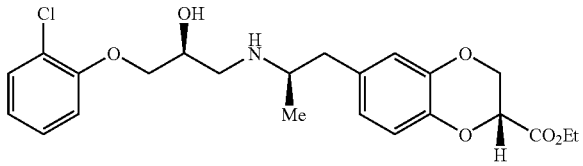

The title compound was prepared using 2-(chlorophenoxy-methyl)-(S)-oxirane in the same manner as in Example 1. Yield: 53%

$^1$H-NMR (CDCl$_3$) δ: 1.08 (d, 3H, J=6.0 Hz), 1.29 (t, 3H, J=6.8 Hz), 2.52 (dd, 1H, J=6.4 Hz, 13.6 Hz), 2.65 (dd, 1H, J=6.8 Hz, 13.6 Hz), 2.83–2.94 (m, 3H), 3.95–4.08 (m, 3H), 4.21–4.41 (m, 4H), 4.79 (dd, 1H, J=3.2 Hz, 5.2 Hz), 6.67–6.74 (m, 2H), 6.87–6.98 (m, 3H), 7.16–7.23 (m, 1H), 7.32–7.38 (m, 1H).

EXAMPLE 8

6-[2-(R)-[2-(S)-Hydroxy-3-(2-chlorophenoxy)propylamino]-propyl]-2,3-dihydro-1,4-benzodioxine-2-(R)-carboxylic acid

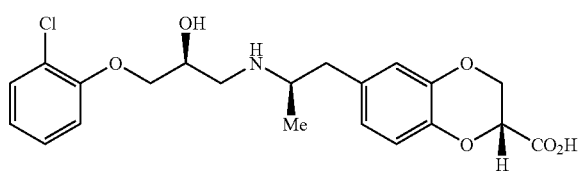

The title compound was prepared using 6-[2-(R)-[3-(2-chlorophenoxy)-2-(S)-hydroxypropylamino]propyl]-2,3-dihydro-1,4-benzodioxine-2-(R)-carboxylic acid ethyl ester obtained in Example 7 in the same manner as in Example 2. Yield: 93%

$^1$H-NMR (DMSO-$d_6$, 40° C.) δ: 0.91 (d, 3H, J=6.8 Hz), 2.14 (t, 1H, J=11.2 Hz), 2.45–2.57 (m, 1H), 2.86–3.05 (m, 3H), 3.96–4.10 (m, 2H), 4.21–4.27 (m, 2H), 4.34 (dd, 1H, J=4.0 Hz, 10.8 Hz), 4.50 (t, 1H, J=3.2 Hz), 6.41–6.54 (m, 2H), 6.73 (d, 1H, J=7.6 Hz), 6.90–6.98 (m, 1H), 7.11–7.18 (m, 1H), 7.25–7.32 (m, 1H), 7.36–7.42 (m, 1H).

EXAMPLE 9

6-[2-(R)-[3-(4-Chlorophenoxy)-2-(S)-hydroxypropylamino]-propyl]-2,3-dihydro-1,4-benzodioxine-2-(R)-carboxylic acid ethyl ester

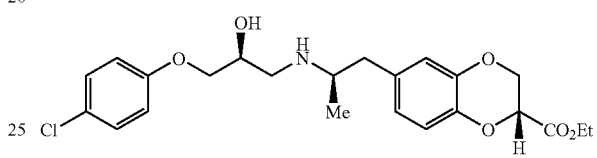

The title compound was prepared using 2-(4-chlorophenoxymethyl)-(S)-oxirane in the same manner as in Example 1. Yield: 42%

$^1$H-NMR (CDCl$_3$) δ: 1.07 (d, 3H, J=6.4 Hz), 1.29 (t, 3H, J=7.6 Hz), 2.54 (dd, 1H, J=6.0 Hz, 13.6 Hz), 2.63 (dd, 1H, J=6.8 Hz, 13.6 Hz), 2.71–2.80 (m, 1H), 2.82–2.95 (m, 1H), 3.88–3.98 (m, 3H), 4.20–4.40 (m, 4H), 4.79 (t, 1H, J=4.0 Hz), 6.67–6.73 (m, 2H), 6.78–6.87 (m, 2H), 6.90–6.95 (m, 1H), 7.19–7.26 (m, 2H).

EXAMPLE 10

6-[2-(R)-[2-(S)-Hydroxy-3-(4-chlorophenoxy)propylamino]-propyl]-2,3-dihydro-1,4-benzodioxine-2-(R)-carboxylic acid

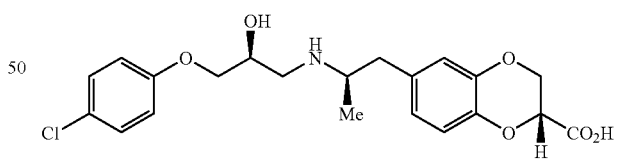

The title compound was prepared using 6-[2-(R)-[3-(4-chlorophenoxy)-2-(S)-hydroxypropylamino]propyl]-2,3-dihydro-1,4-benzodioxine-2-(R)-carboxylic acid ethyl ester obtained in Example 9 in the same manner as in Example 2. Yield: 70%

$^1$H-NMR (DMSO-$d_6$, 40° C.) δ: 0.88 (d, 3H, J=6.0 Hz), 1.99–2.11 (m, 1H), 2.36–2.47 (m, 1H), 2.79–3.05 (m, 3H), 3.93 (d, 2H, J=5.2 Hz), 4.11–4.28 (m, 2H), 4.34–4.44 (m, 1H), 4.49–4.57 (m, 1H), 6.38 (brd, 1H, J=8.0 Hz), 6.45 (brs, 1H), 6.72 (d, 1H, J=8.0 Hz), 6.96 (d, 2H, J=8.8 Hz), 7.30 (d, 2H, J=8.8 Hz).

EXAMPLE 11

6-[2-(R)-[3-(4-Benzyloxyphenoxy)-2-(S)-hydroxypropylamino]-propyl]-2,3-dihydro-1,4-benzodioxine-2-(R)-carboxylic acid ethyl ester

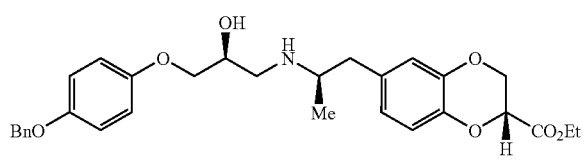

The title compound was prepared using 2-(4-benzyloxy)-(S)-oxirane in the same manner as in Example 1. Yield: 43%

$^1$H-NMR (CDCl$_3$) δ: 1.09 (d, 3H, J=6.4 Hz), 1.23–1.34 (m, 3H), 2.55 (dd, 1H, J=6.8 Hz, 13.2 Hz), 2.69 (dd, 1H, J=6.4 Hz, 13.2 Hz), 2.80 (dd, 1H, J=4.4 Hz, 8.4 Hz), 2.84–3.00 (m, 2H), 3.86–4.03 (m, 3H), 4.21–4.33 (m, 2H), 4.33–4.40 (m, 2H), 4.78 (t, 1H, J=4.0 Hz), 5.01 (s, 2H), 6.68–6.73 (m, 2H), 6.79–6.86 (m, 2H), 6.86–6.96 (m, 3H), 7.28–7.45 (m, 5H).

EXAMPLE 12

6-[2-(R)-[2-(S)-Hydroxy-3-(4-hydroxyphenoxy)propylamino]-propyl]-2,3-dihydro-1,4-benzodioxine-2-(R)-carboxylic acid

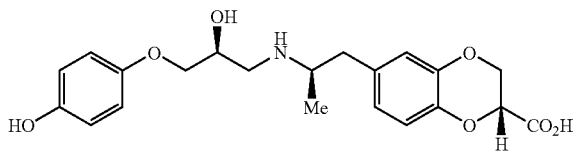

To a solution of 6-[2-(R)-[3-(4-benzyloxyphenoxy)-2-(S)-hydroxypropylamino]propyl-2,3-dihydro-1,4-benzodioxine-2-(R)-carboxylic acid ethyl ester obtained in Example 11 (270 mg) in ethanol (20 mL) was added 10% palladium-carbon (50 mg). This solution was stirred under hydrogen atmosphere at room temperature for 16 hours. After filtration through Celite, the filtrate was concentrated under reduced pressure. A solution of the residue in 1N—HCl (8 mL) was stirred at 100° C. for 5 hours. After allowing to cool to room temperature, it was concentrated to dryness under reduced pressure. The residue was dissolved in water/acetonitrile=1/1 (v/v) (10 mL), and the pH was adjusted to 6.3 by addition of saturated aqueous sodium bicarbonate. It was concentrated under reduced pressure, the residue was purified by HP column chromatography and the title compound (209 mg) was obtained from the effluent with water/methanol=40/60 (v/v). Yield: 85%

$^1$H-NMR (DMSO-d$_6$, 40° C.) δ: 0.90 (d, 3H, J=5.6 Hz), 2.09–2.21 (m, 1H), 2.53–3.05 (m, 4H), 3.70–3.90 (m, 2H), 4.07–4.40 (m, 3H), 4.42–4.54 (m, 1H), 6.40–6.79 (m, 7H).

EXAMPLE 13

6-[2-(R)-[2-(S)-Hydroxy-3-(4-methoxyphenoxy)propylamino]-propyl]-2,3-dihydro-1,4-benzodioxine-2-(R)-carboxylic acid ethyl ester

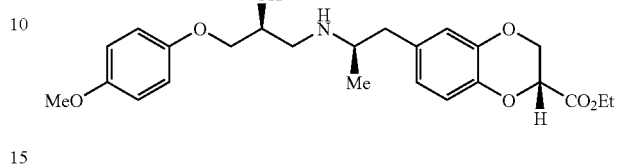

The title compound was prepared using 2-(4-methoxyphenoxymethyl)-(S)-oxirane in the same manner as in Example 1. Yield: 61%

$^1$H-NMR (CDCl$_3$) δ: 1.10 (d, 3H, J=6.0 Hz), 1.22–1.34 (m, 3H), 2.55 (dd, 1H, J=6.4 Hz, 13.6 Hz), 2.71 (dd, 1H, J=6.4 Hz, 13.6 Hz), 2.81 (dd, 1H, J=8.0 Hz, 12.8 Hz), 2.86–2.98 (m, 2H), 3.76 (s, 3H), 3.87–4.02 (m, 3H), 4.21–4.39 (m, 4H), 4.79 (dd, 1H, J=3.6 Hz, 4.4 Hz), 6.67–6.74 (m, 2H), 6.79–6.87 (m, 4H), 6.90–6.94 (m, 1H).

EXAMPLE 14

6-[2-(R)-[2-(S)-Hydroxy-3-(4-methoxyphenoxy)propylamino]-propyl]-2,3-dihydro-1,4-benzodioxine-2-(R)-carboxylic acid

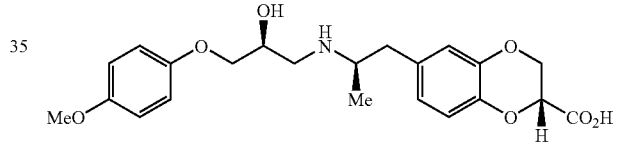

The title compound was prepared using 6-[2-(R)-[2-(S)-hydroxy-3-(4-methoxyphenoxy)propylamino]propyl]-2,3-dihydro-1,4-benzodioxine-2-(R)-carboxylic acid ethyl ester obtained in Example 13 in the same manner as in Example 2. Yield: 63%

$^1$H-NMR (DMSO-d$_6$, 40° C.) δ: 0.86 (d, 3H, J=6.8 Hz), 1.98 (t, 1H, J=12.0 Hz), 2.30–2.42 (m, 1H), 2.84–3.09 (m, 3H), 3.70 (s, 3H), 3.81–3.97 (m, 2H), 4.08–4.17 (m, 1H), 4.23–4.33 (m, 1H), 4.43–4.50 (m, 1H), 4.56–4.64 (m, 1H), 6.33 (d, 1H, J=8.0 Hz), 6.41 (s, 1H), 6.72 (d, 1H, J=8.0 Hz), 6.80–6.95 (m, 4H).

EXAMPLE 15

6-[2-(R)-[3-(4-Benzyloxy-2-methoxyphenoxy)-2-(S)-hydroxypropylamino]propyl]-2,3-dihydro-1,4-benzodioxine-2-(R)-carboxylic acid ethyl ester

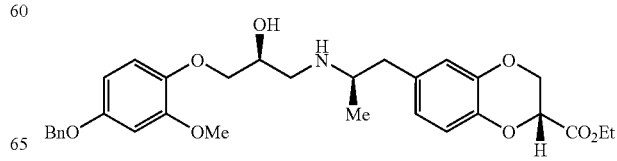

The title compound was prepared using 2-(4-benzyloxy-2-methoxyphenoxymethyl)-(S)-oxirane obtained in Preparation Example 5 in the same manner as in Example 1. Yield: 37%

¹H-NMR (CDCl₃) δ: 1.08 (d, 3H, J=6.0 Hz), 1.28 (t, 3H, J=6.8 Hz), 2.51 (dd, 1H, J=6.8 Hz, 11.2 Hz), 2.72 (dd, 1H, J=6.4 Hz, 13.2 Hz), 2.79–2.97 (m, 3H), 3.81 (s, 3H), 3.88–4.04 (m, 3H), 4.21–4.31 (m, 2H), 4.32–4.39 (m, 2H), 4.78 (dd, 1H, J=2.8 Hz, 4.4 Hz), 5.01 (s, 2H), 6.45 (dd, 1H, J=3.2 Hz, 8.8 Hz), 6.58 (d, 1H, J=3.2 Hz), 6.67–6.73 (m, 2H), 6.84 (d, 1H, J=8.4 Hz), 6.94 (d, 1H, J=8.4 Hz), 7.29–7.46 (m, 5H).

EXAMPLE 16

6-[2-(R)-[2-(S)-Hydroxy-3-(4-hydroxy-2-methoxyphenoxy)-propylamino]propyl]-2,3-dihydro-1,4-benzodioxine-2-(R)-carboxylic acid

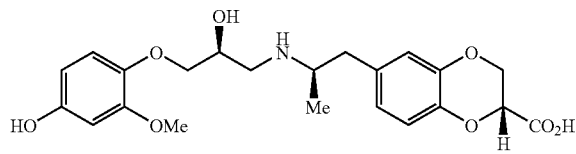

The title compound was prepared using 6-[2-(R)-[3-(4-benzyloxy-2-methoxyphenoxy)-2-(S)-hydroxypropylamino]propyl]-2,3-dihydro-1,4-benzodioxine-2-(R)-carboxylic acid ethyl ester obtained in Preparation Example 15 in the same manner as in Example 12. Yield: 81%

¹H-NMR (DMSO-d₆, 40° C.) δ: 0.90 (d, 3H, J=6.4 Hz), 2.17 (t, 1H, J=11.2 Hz), 2.44–2.59 (m, 1H), 2.72–3.01 (m, 3H), 3.61–3.88 (m, 2H), 3.70 (s, 3H), 3.99–4.35 (m, 3H), 4.40–4.49 (m, 1H), 6.24 (dd, 1H, J=2.8 Hz, 8.8 Hz), 6.41 (d, 1H, J=2.8 Hz), 6.44–6.53 (m, 2H), 6.72–6.77 (m, 2H).

EXAMPLE 17

6-[2-[3-(4-Benzyloxy-2-methoxyphenoxy)-2-(S)-hydroxypropylamino]ethyl-2,3-dihydro-1,4-benzodioxine-2-(R)-carboxylic acid ethyl ester

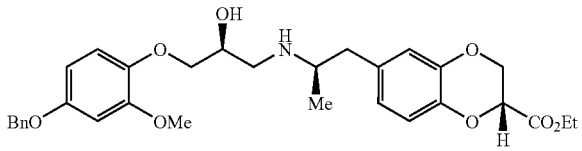

The title compound was prepared using 2-(4-benzyloxy-2-methoxyphenoxymethyl)-(S)-oxirane obtained in Preparation Example 5 in the same manner as in Example 3. Yield: 34%

¹H-NMR (CDCl₃) δ: 1.28 (t, 3H, J=7.2 Hz), 2.64–2.98 (m, 6H), 3.79 (s, 3H), 3.88–4.08 (m, 3H), 4.21–4.30 (m, 2H), 4.34 (d, 2H, J=3.6 Hz), 4.77 (t, 1H, J=3.6 Hz), 4.99 (s, 2H), 6.44 (dd, 1H, J=3.2 Hz, 8.8 Hz), 6.57 (d, 1H, J=3.2 Hz), 6.66–6.74 (m, 2H), 6.81–6.86 (m, 1H), 6.88–6.93 (m, 1H), 7.28–7.44 (m, 5H).

EXAMPLE 18

6-[2-[2-(S)-Hydroxy-3-(4-hydroxy-2-methoxyphenoxy)-propylamino]ethyl]-2,3-dihydro-1,4-benzodioxine-2-(R)-carboxylic acid ethyl ester

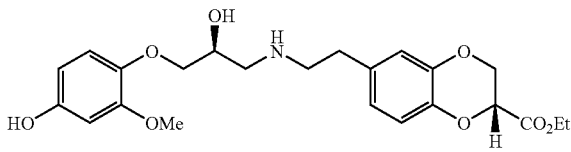

To a solution of 6-[2-[3-(4-benzyloxy-2-methoxyphenoxy)-2-(S)-hydroxypropylamino]ethyl]-2,3-dihydro-1,4-benzodioxine-2-(R)-carboxylic acid ethyl ester obtained in Example 17 (240 mg) in ethanol (10 mL) was added 10% palladium-carbon (24 mg). This solution was stirred under hydrogen atmosphere at room temperature for 6 hours. After filtration through Celite, the filtrate was concentrated under reduced pressure. The residue was purified by column chromatography on silica gel and the title compound (129 mg) was obtained from the effluent with chloroform/methanol/aqueous ammonia=85/15/0.1 (v/v). Yield: 64%

¹H-NMR (CDCl₃) δ: 1.29 (t, 3H, J=6.8 Hz), 2.80–3.07 (m, 6H), 3.73 (m, 3H), 3.86–3.98 (m, 2H), 4.12–4.20 (m, 1H), 4.22–4.31 (m, 2H), 4.33 (d, 2H, J=4.0 Hz), 4.77 (t, 1H, J=4.0 Hz), 6.26–6.31 (m, 1H), 6.39–6.43 (m, 1H), 6.63–6.74 (m, 3H), 6.86–6.91 (m, 1H).

EXAMPLE 19

6-[2-(2-(S)-Hydroxy-3-(4-hydroxy-2-methoxyphenoxy)propyl-amino]ethyl]-2,3-dihydro-1,4-benzodioxine-2-(R)-carboxylic acid

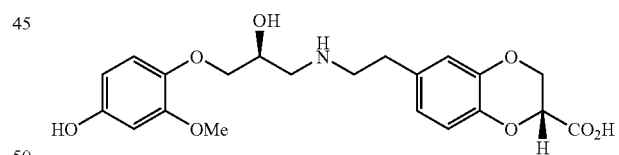

The title compound was prepared using 6-[2-[2-(S)-hydroxy-3-(4-hydroxy-2-methoxyphenoxy)propylamino] ethyl]-2,3-dihydro-1,4-benzodioxine-2-carboxylic acid ethyl ester obtained in Example 18 (129 mg) in the same manner as in Example 2. Yield: 82%

¹H-NMR (DMSO-d₆, 40° C.) δ: 2.42–2.59 (m, 2H), 2.72–2.92 (m, 3H), 2.99–3.07 (m, 1H), 3.70 (s, 3H), 3.75 (dd, 1H, J=6.4 Hz, 10.4 Hz), 3.83 (dd, 1H, J=5.2 Hz, 10.4 Hz), 4.02–4.11 (m, 1H), 4.15 (dd, 1H, J=2.8 Hz, 11.2 Hz), 4.41 (dd, 1H, J=3.2 Hz, 11.2 Hz), 4.51 (t, 1H, J=3.2 Hz), 6.23 (dd, 1H, J=2.8 Hz, 8.4 Hz), 6.41 (d, 1H, J=2.8 Hz), 6.51 (dd, 1H, J=2.0 Hz, 8.4 Hz), 6.58 (d, 1H, J=2.0 Hz), 6.74 (d, 1H, J=8.4 Hz), 6.76 (d, 1H, J=8.4 Hz).

EXAMPLE 20

6-[2-(R)-[3-(2-Chloro-4-(methoxymethoxy)phenoxy]-2-(S)-hydroxypropylamino]propyl]-2,3-dihydro-1,4-benzodioxine-2-(R)-carboxylic acid ethyl ester

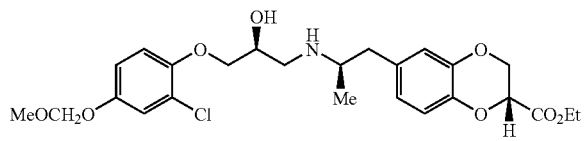

The title compound was prepared using 2-[2-chloro-4-(methoxymethoxy)phenoxymethyl]-(S)-oxirane obtained in Preparation Example 6 in the same manner as in Example 1. Yield: 48%

$^1$H-NMR (CDCl$_3$) δ: 1.09 (d, 3H, J=6.0 Hz), 1.29 (t, 3H, J=7.2 Hz), 2.53 (dd, 1H, J=6.8 Hz, 9.6 Hz), 2.71 (dd, 1H, J=6.8 Hz, 9.6 Hz), 2.78–3.04 (m, 3H), 3.47 (s, 3H), 3.92–4.07 (m, 3H), 4.21–4.40 (m, 4H), 4.79 (dd, 1H, J=3.6 Hz, 4.8 Hz), 5.09 (s, 2H), 6.67–6.73 (m, 2H), 6.83–6.93 (m, 3H), 7.07–7.12 (m, 1H).

EXAMPLE 21

6-[2-(R)-[2-(S)-Hydroxy-3-(2-chloro-4-hydroxyphenoxy)-propylamino]propyl]-2,3-dihydro-1,4-benzodioxine-2-(R)-carboxylic acid

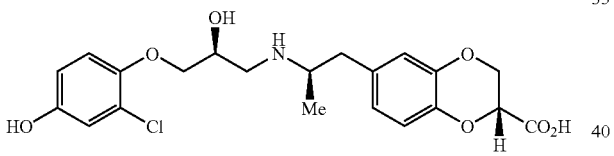

The title compound was prepared using 6-[2-(R)-[3-[2-chloro-4-(methoxymethoxy)phenoxy]-2-(S)-hydroxypropylamino]-propyl]-2,3-dihydro-1,4-benzodioxine-2-(R)-carboxylic acid ethyl ester obtained in Example 20 in the same manner as in Example 2. Yield: 81%

EXAMPLE 22

6-[2-[3-(2-Chloro-4-(methoxymethoxy)phenoxy]-2-(S)-hydroxypropylamino]ethyl]-2,3-dihydro-1,4-benzodioxine-2-(R)-carboxylic acid ethyl ester

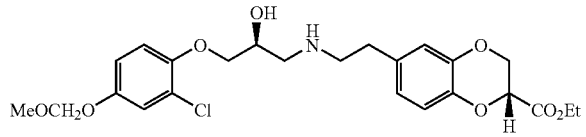

The title compound was prepared using 2-[2-chloro-4-(methoxymethoxy)phenoxymethyl]-(S)-oxirane obtained in Preparation Example 6 in the same manner as in Example 3. Yield: 54%

$^1$H-NMR (CDCl$_3$) δ: 1.29 (t, 3H, J=6.8 Hz), 2.56–2.80 (m, 2H), 2.82–2.96 (m, 4H), 3.47 (s, 3H), 3.95–4.02 (m, 2H), 4.03–4.10 (m, 1H), 4.21–4.32 (m, 2H), 4.34–4.39 (m, 2H), 4.79 (t, 1H, J=4.0 Hz), 5.09 (s, 2H), 6.70–6.75 (m, 2H), 6.84–6.95 (m, 3H), 7.08–7.11 (m, 1H).

EXAMPLE 23

6-[2-[2-(S)-Hydroxy-3-(2-chloro-4-hydroxyphenoxy]-propylamino]ethyl]-2,3-dihydro-1,4-benzodioxine-2-(R)-carboxylic acid

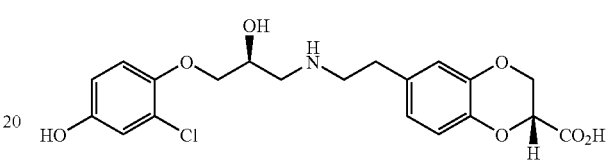

The title compound was prepared using 6-[2-[3-(2-chloro-4-(methoxymethoxy)phenoxy]-2-(S)-hydroxypropylamino] ethyl]-2,3-dihydro-1,4-benzodioxine-2-(R)-carboxylic acid ethyl ester obtained in Example 22 in the same manner as in Example 2. Yield: 62%

$^1$H-NMR (DMSO-d$_6$, 40° C.) δ: 2.38–2.55 (m, 2H), 2.71–2.91 (m, 3H), 2.99–3.06 (m, 1H), 3.86 (dd, 1H, J=5.6 Hz, 10.0 Hz), 3.92 (dd, 1H, J=5.2 Hz, 10.0 Hz), 4.07–4.18 (m, 2H), 4.41 (dd, 1H, J=3.2 Hz, 10.8 Hz), 4.52 (t, 1H, J=3.2 Hz), 6.50 (dd, 1H, J=2.0 Hz, 8.0 Hz), 6.58 (d, 1H, J=2.0 Hz), 6.66 (dd, 1H, J=3.2 Hz, 9.2 Hz), 6.73 (d, 1H, J=8.0 Hz), 6.80 (d, 1H, J=3.2 Hz), 6.96 (d, 1H, J=9.2 Hz).

EXAMPLE 24

6-[2-(R)-[3-[3-Chloro-4-(methoxymethoxy)phenoxy]-2-(S)-hydroxypropylamino]propyl]-2,3-dihydro-1,4-benzodioxine-2-(R)-carboxylic acid ethyl ester

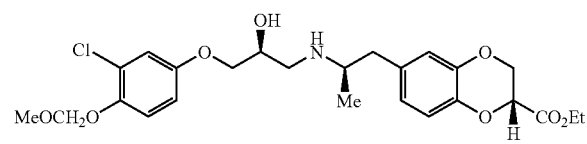

The title compound was prepared using 2-[3-chloro-4-(methoxymethoxy)phenoxymethyl]-(S)-oxirane obtained in Preparation Example 7 in the same manner as in Example 1. Yield: 34%

$^1$H-NMR (CDCl$_3$) δ: 1.08 (d, 3H, J=7.6 Hz), 1.29 (t, 3H, J=7.6 Hz), 2.55 (dd, 1H, J=6.4 Hz, 9.6 Hz), 2.66 (dd, 1H, J=7.2 Hz, 9.6 Hz), 2.75 (dd, 1H, J=8.0 Hz, 12.4 Hz), 2.82–2.96 (m, 2H), 3.53 (s, 3H), 3.86–4.00 (m, 3H), 4.20–4.32 (m, 2H), 4.34–4.40 (m, 2H), 4.79 (t, 1H, J=4.0 Hz), 5.16 (s, 2H), 6.68–6.78 (m, 3H), 6.90–6.97 (m, 2H), 7.06–7.11 (m, 1H).

EXAMPLE 25

6-[2-(R)-2-(S)-Hydroxy-3-(3-chloro-4-hydroxyphenoxy)propyl-amino]propyl]-2,3-dihydro-1,4-benzodioxine-2-(R)-carboxylic acid

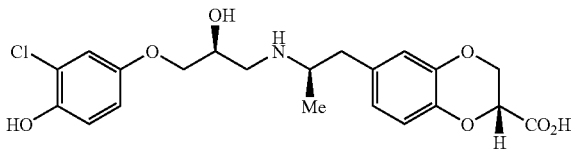

The title compound was prepared using 6-[2-(R)-[3-[3-chloro-4-(methoxymethoxy)phenoxy]-2-(S)-hydroxypropylamino]-propyl]-2,3-dihydro-1,4-benzodioxine-2-(R)-carboxylic acid ethyl ester obtained in Example 24 in the same manner as in Example 2. Yield: 80%

$^1$H-NMR (DMSO-d$_6$, 40° C.) δ: 0.88 (d, 3H, J=7.2 Hz), 2.02 (t, 1H, J=12.0 Hz), 2.38–2.47 (m, 1H), 2.85–3.13 (m, 3H), 3.77–3.95 (m, 2H), 4.12 (dd, 1H, J=2.8 Hz, 10.8 Hz), 4.22–4.33 (m, 1H), 4.56 (dd, 1H, J=2.4 Hz, 10.8 Hz), 4.61 (t, 1H, J=2.4 Hz), 6.33–6.38 (m, 1H), 6.42–6.45 (m, 1H), 6.70–6.78 (m, 2H), 6.84–6.70 (m, 2H).

EXAMPLE 26

6-[2-(R)-[2-(S)-Hydroxy-3-[3-methanesulfonamido-5-methoxy-4-(methoxymethoxy)phenoxy]propylamino]propyl]-2,3-dihydro-1,4-benzodioxine-2-(R)-carboxylic acid ethyl ester

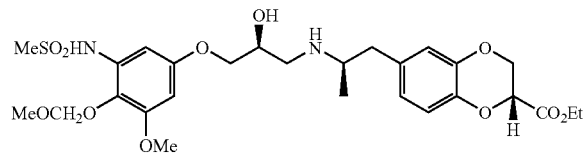

The title compound was prepared using N-[3-methoxy-2-methoxymethoxy-5-(S)-oxiranylmethoxyphenyl]methane-sulfonamide obtained in Preparation Example 9 in the same manner as in Example 1. Yield: 32%

$^1$H-NMR (CDCl$_3$) δ: 1.10 (d, 3H, J=6.4 Hz), 1.29 (t, 3H, J=7.2 Hz), 2.55 (dd, 1H, J=6.8 Hz, 13.6 Hz), 2.69–2.81 (m, 2H), 2.86–3.00 (m, 2H), 2.97 (s, 3H), 3.54 (s, 3H), 3.82 (s, 3H), 3.89–4.04 (m, 3H), 4.20–4.41 (m, 4H), 4.80 (dd, 1H, J=3.6 Hz, 4.4 Hz), 5.01 (s, 2H), 6.36 (d, 1H, J=2.8 Hz), 6.68–6.73 (m, 2H), 6.75 (d, 1H, J=2.8 Hz), 6.89–6.94 (m, 1H).

EXAMPLE 27

6-[2-(R)-[2-(S)-Hydroxy-3-(4-hydroxy-3-methane-sulfonamido-5-methoxyphenoxy)propylamino]propyl]-2,3-dihydro-1,4-benzodioxine-2-(R)-carboxylic acid ethyl ester hydrochloride

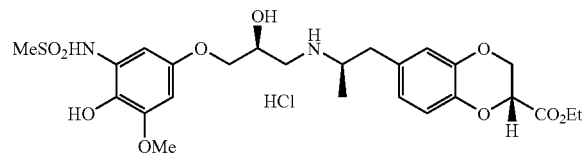

To a solution of 6-[2-(R)-[2-(S)-hydroxy-3-[3-methane-sulfonamido-5-methoxy-4-(methoxymethoxy)phenoxy]- propylamino]propyl]-2,3-dihydro-1,4-benzodioxine-2-(R)-carboxylic acid ethyl ester (100 mg) obtained in Example 26 in ethanol (10 mL) was added 4N—HCl/AcOEt (1.0 mL, 4.0 mmol) at room temperature. This solution was stirred at room temperature for 16 hours and then concentrated to dryness under reduced pressure, affording the title compound (100 mg). Yield: 85%

$^1$H-NMR (DMSO-d$_6$, 40° C.) δ: 1.12 (d, 3H, J=6.4 Hz), 1.19 (t, 3H, J=7.2 Hz), 2.42–2.62 (m, 2H), 2.94 (s, 3H), 3.01–3.13 (m, 2H), 3.15–3.24 (m, 1H), 3.38–3.49 (m, 1H), 3.80 (s, 3H), 3.87–3.95 (m, 2H), 4.16 (q, 2H, J=7.2 Hz), 4.28 (dd, 1H, J=3.2 Hz, 12.0 Hz), 4.41 (dd, 1H, J=3.6 Hz, 12.0 Hz), 5.12 (t, 1H, J=3.2 Hz), 5.76–5.82 (m, 1H), 6.49 (s, 2H), 6.72–6.80 (m, 2H), 6.90–6.93 (m, 1H).

EXAMPLE 28

6-[2-(R)-[2-(S)-Hydroxy-3-(4-amino-3,5-dichlorophenoxy)-propylamino]propyl]-2,3-dihydro-1,4-benzodioxine-2-(R)-carboxylic acid ethyl ester

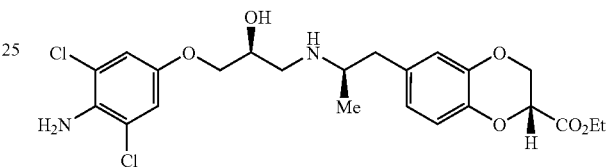

The title compound was prepared using 2,6-dichloro-4-oxiranylmethoxyphenylamine obtained in Preparation Example 10 in the same manner as in Example 1. Yield: 30%

$^1$H-NMR (CDCl$_3$) δ: 1.09 (d, 3H, J=6.4 Hz), 1.29 (t, 3H, J=7.2 Hz), 2.55 (dd, 1H, J=6.4 Hz, 14.0 Hz), 2.67 (dd, 1H, J=7.2 Hz, 14.0 Hz), 2.74 (dd, 1H, J=8.0 Hz, 16.0 Hz), 2.78–2.98 (m, 3H), 3.85 (d, 1H, J=5.2 Hz), 3.90–3.99 (m, 1H), 4.11 (brs, 2H), 4.21–4.32 (m, 2H), 4.35–4.39 (m, 2H), 4.79 (dd, 1H, J=3.6 Hz, 4.4 Hz), 6.68–6.73 (m, 2H), 6.83 (s, 2H), 6.92 (d, 1H, J=8.0 Hz).

EXAMPLE 29

6-[2-(R)-[2-(S)-Hydroxy-3-(4-amino-3,5-dichlorophenoxy)-propylamino]propyl]-2,3-dihydro-1,4-benzodioxine-2-(R)-carboxylic acid

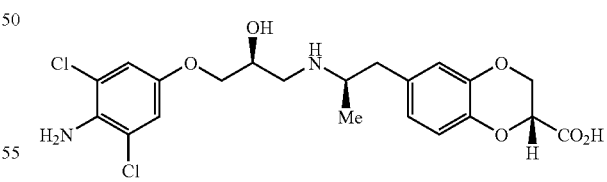

The title compound was prepared using 6-[2-(R)-2-(S)-hydroxy-3-(4-amino-3,5-dichlorophenoxy)-propylamino] propyl]-2,3-dihydro-1,4-benzodioxine-2-(R)-carboxylic acid ethyl ester obtained in Example 28 in the same manner as in Example 2. Yield: 64%

$^1$H-NMR (DMSO-d$_6$, 40° C.) δ: 0.89 (d, 3H, J=6.0 Hz), 2.09–2.21 (m, 1H), 2.70–2.99 (m, 4H), 3.78–3.92 (m, 2H), 3.98–4.09 (m, 1H), 4.17–4.34 (m, 2H), 4.39–4.50 (m, 1H), 4.89 (s, 2H), 6.45 (d, 1H, J=8.0 Hz), 6.51 (s, 1H), 6.72 (d, 1H, J=8.0 Hz), 6.94 (s, 2H).

EXAMPLE 30

6-[2-[2-(S)-Hydroxy-3-(4-amino-3,5-dichlorophenoxy)-propylamino]ethyl]-2,3-dihydro-1,4-benzodioxine-2-(R)-carboxylic acid ethyl ester

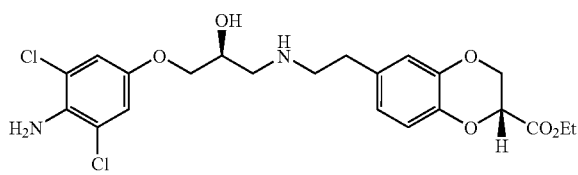

The title compound was prepared using 2,6-dichloro-4-(S)-oxiranylmethoxyphenylamine obtained in Preparation Example 10 in the same manner as in Example 3. Yield: 51%

$^1$H-NMR (CDCl$_3$) δ: 1.29 (t, 3H, J=7.2 Hz), 2.64–2.97 (m, 6H), 3.85 (d, 2H, J=5.2 Hz), 3.95–4.04 (m, 1H), 4.11 (brs, 2H), J=3.6 Hz), 6.66–6.77 (m, 2H), 6.82 (s, 2H), 6.90–6.96 (m, 1H).

EXAMPLE 31

6-[2-[2-(S)-Hydroxy-3-(4-amino-3,5-dichlorophenoxy)-propylamino]ethyl]-2,3-dihydro-1,4-benzodioxine-2-(R)-carboxylic acid

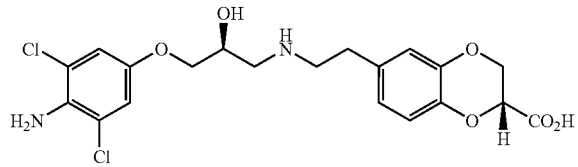

The title compound was prepared using 6-[2-[2-(S)-hydroxy-3-(4-amino-3,5-dichlorophenoxy)-propylamino]ethyl]- 2,3-dihydro-1,4-benzodioxine-2-(R)-carboxylic acid ethyl ester obtained in Example 30 in the same manner as in Example 2. Yield: 79%

$^1$H-NMR (DMSO-d$_6$, 40° C.) δ: 2.64–2.89 (m, 3H), 2.91–3.01 (m, 1H), 3.07–3.54 (m, 2H), 3.86 (d, 2H, J=5.2 Hz), 4.01–4.11 (m, 1H), 4.12–4.21 (m, 1H), 4.36–4.45 (m, 1H), 4.46–4.55 (m, 1H), 4.91 (s, 2H), 6.50 (d, 1H, J=8.0 Hz), 6.58 (s, 1H), 6.73 (d, 1H, J=8.0 Hz), 6.94 (s, 2H).

EXAMPLE 32

6-[2-(R)-[2-(S)-Hydroxy-3-(5-chloropyridin-3-yloxy)-propylamino]propyl]-2,3-dihydro-1,4-benzodioxine-2-(R)-carboxylic acid ethyl ester

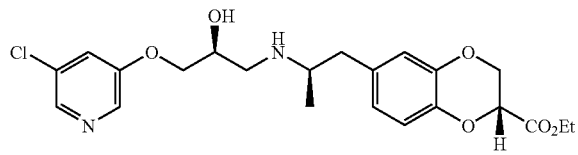

The title compound was prepared using 3-chloro-5-(S)-oxiranylmethoxypyridine obtained in Preparation Example 11 in the same manner as in Example 1. Yield: 39%

$^1$H-NMR (CDCl$_3$) δ: 1.09 (d, 3H, J=6.3 Hz), 1.29 (t, 3H, J=7.1 Hz), 1.89 (brs, 2H), 2.52–2.65 (m, 2H), 2.74 (dd, 1H, J=7.8 Hz, 12 Hz), 2.81–2.92 (m, 2H), 3.89–3.99 (m, 1H), 3.99 (d, 2H, J=4.4 Hz), 4.21–4.32 (m, 2H), 4.38 (dd, 2H, J=1.0 Hz, 3.4 Hz), 4.80 (t, 1H, J=7.8 Hz), 6.67–6.74 (m, 2H), 6.93 (d, 1H, J=8.8 Hz), 7.24 (t, 1H, J=2.2 Hz), 8.19 (d, 1H, J=2.0 Hz), 8.21 (d, 1H, J=2.4 Hz).

EXAMPLE 33

6-[2-(R)-[2-(S)-Hydroxy-3-(5-chloropyridin-3-yloxy)-propylamino]propyl]-2,3-dihydro-1,4-benzodioxine-2-(R)-carboxylic acid

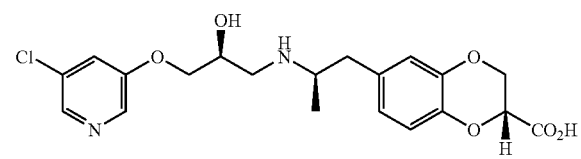

The title compound was prepared using 6-[2-(R)-[3-(5-chloropyridin-3-yloxy)propylamino]propyl]-2,3-dihydro-1,4-benzodioxine-2-(R)-carboxylic acid ethyl ester obtained in Example 32 in the same manner as in Example 2. Yield: 68%

$^1$H-NMR (DMSO-d$_6$) δ: 0.89 (d, 3H, J=6.3 Hz), 2.04–2.13 (m, 1H), 2.45–2.51 (m, 1H), 2.78–3.01 (m, 3H), 3.24 (brs, 2H), 3.93–4.12 (m, 3H), 4.12–4.22 (m, 2H), 4.36 (br d, 1H, J=8.8 Hz), 4.52 (s, 1H), 6.42 (br d, 1H, J=8.3 Hz), 6.47 (brs, 1H), 6.73 (d, 1H, J=8.3 Hz), 7.58 (t, 1H, J=2.2 Hz), 8.19 (d, 1H, J=2.0 Hz), 8.26 (d, 1H, J=2.4 Hz).

EXAMPLE 34

6-[2-(R)-[2-(S)-Hydroxy-3-(1H-5-indolyloxy)propylamino]-propyl]-2,3-dihydro-1,4-benzodioxine-2-(R)-carboxylic acid ethyl ester

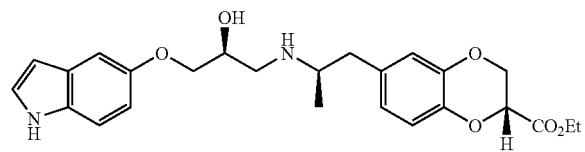

The title compound was prepared using 5-(R)-oxiranylmethoxy-1H-indole obtained in Preparation Example 12 in the same manner as in Example 1. Yield: 34%

$^1$H-NMR (CDCl$_3$) δ: 1.08 (d, 3H, J=6.3 Hz), 1.28 (t, 3H, J=7.1 Hz), 1.95 (brs, 2H), 2.53-(dd, 1H, J=6.6 Hz, 13.0 Hz), 2.66 (dd, 1H, J=6.6 Hz, 13.0 Hz), 2.77–2.94 (m, 3H), 3.95–4.03 (m, 3H), 4.22–4.39 (m, 4H), 4.81 (dd, 1H, J=3.2 Hz, 4.4 Hz), 6.45–6.49 (m, 1H), 6.66–6.75 (m, 2H), 6.86 (dd, 1H, J=2.0 Hz, 8.8 Hz), 6.89–6.95 (m, 1H), 7.10 (d, 1H, J=2.4 Hz), 7.19 (t, 1H, J=2.9 Hz), 7.23–7.28 (m, 1H), 8.09 (brs, 1H).

EXAMPLE 35

6-[2-(R)-[2-(S)-Hydroxy-3-(1H-4-indolyloxy)propylamino]-propyl]-2,3-dihydro-1,4-benzodioxine-2-(R)-carboxylic acid ethyl ester

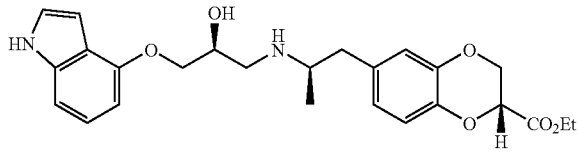

The title compound was prepared using 4-(S)-oxiranylmethoxy-1H-indole obtained in Preparation Example 13 in the same manner as in Example 1. Yield: 51%

$^1$H-NMR (CDCl$_3$) δ: 1.08 (d, 3H, J=6.3 Hz), 1.28 (t, 3H, J=7.1 Hz), 1.95 (brs, 2H), 2.53 (dd, 1H, J=6.8 Hz, 13.0 Hz), 2.68 (dd, 1H, J=6.8 Hz, 13.0 Hz), 2.84–2.98 (m, 3H), 4.04–4.19 (m, 3H), 4.22–4.32 (m, 2H), 4.32–4.39 (m, 2H), 4.78 (dd, 1H, J=3.4 Hz, 4.9 Hz), 6.52 (d, 1H, J=7.8 Hz), 6.63 (t, 1H, J=2.2 Hz), 6.68–6.73 (m, 2H), 6.92 (d, 1H, J=8.8 Hz), 7.03 (d, 1H, J=8.3 Hz), 7.09 (t, 1H, J=7.8 Hz), 7.12 (t, 1H, J=2.7 Hz), 8.18 (s, 1H).

PREPARATION EXAMPLE 1

2-Methoxymethoxy-5-(S)-oxiranylmethoxyaniline

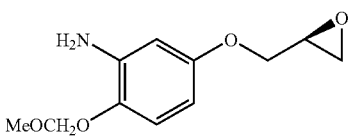

To a solution of 3-amino-4-(methoxymethoxy)phenol (1.67 g) in acetone (50 mL) were added potassium carbonate (2.0 g) and (2S)-(+)-glycidyl-3-nitrobenzenesulfonate (2.69 g). This solution was stirred under reflux for 48 hours and then concentrated under reduced pressure. To the residue were added water and ethyl acetate followed by separation of liquid phases. The oily phase was washed with water and brine in turn, dried over anhydrous sodium sulfate and concentrated under reduced pressure. The residue was purified by column chromatography on silica gel and the title compound (430 mg) was obtained from the effluent with chloroform/ethyl acetate=85/15 (v/v). Yield: 19%

$^1$H-NMR (CDCl$_3$) δ: 2.72 (dd, 1H, J=2.4 Hz, 4.8 Hz), 2.88 (t, 1H, J=4.8 Hz), 3.28–3.34 (m, 1H), 3.49 (s, 3H), 3.80–3.93 (m, 3H), 4.11 (dd, 1H, J=3.2 Hz, 11.2 Hz), 5.11 (s, 2H), 6.22 (dd, 1H, J=2.8 Hz, 8.4 Hz), 6.35 (d, 1H, J=2.8 Hz), 6.91 (d, 1H, J=8.4 Hz).

PREPARATION EXAMPLE 2

N-[2-Methoxymethoxy-5-(S)-oxiranylmethoxyphenyl]-methanesulfonamide

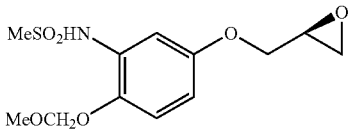

To a solution of 2-methoxymethoxy-5-(S)-oxiranylmethoxyaniline obtained in Preparation Example 1 (430 mg) in pyridine (10 mL) was added methanesulfonyl chloride (0.22 mL) under ice cooling. This solution was stirred under ice cooling for 1.5 hours and ethyl acetate was then added. The solution was washed with 3N—HCl (twice), saturated aqueous sodium hydrogencarbonate and brine in turn, dried over anhydrous sodium sulfate and then concentrated under reduced pressure. The residue was purified by column chromatography on silica gel and the title compound (510 mg) was obtained from the effluent with hexane/ethyl acetate=50/50 (v/v). Yield: 88%

$^1$H-NMR (CDCl$_3$) δ: 2.76 (dd, 1H, J=2.8 Hz, 4.8 Hz), 2.90 (t, 1H, J=4.8 Hz), 3.00 (s, 3H), 3.30–3.36 (m, 1H), 3.49 (s, 3H), 3.89 (dd, 1H, J=5.2 Hz, 10.4 Hz), 4.22 (dd, 1H, J=2.8 Hz, 10.8 Hz), 5.15 (s, 2H), 6.65 (dd, 1H, J=2.8 Hz, 9.2 Hz), 7.01 (brs, 1H), 7.07 (d, 1H, J=9.2 Hz), 7.17 (d, 1H, J=2.8 Hz).

PREPARATION EXAMPLE 3

6-(2-Nitrovinyl)-2,3-dihydro-1,4-benzodioxine-2-(R)-carboxylic acid ethyl ester

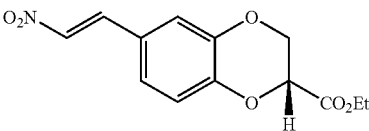

To a solution of 6-formyl-2,3-dihydro-1,4-benzodioxine-2-(R)-carboxylic acid ethyl ester (2.36 g) in benzene (40 mL) was added cyclohexylamine (1.04 g) at room temperature. This solution was stirred under reflux for 2 hours while being dehydrated by means of a Dean-Stark trap, and concentrated under reduced pressure. To a solution of the residue in acetic acid (10 mL) was added nitromethane (0.81 mL) at room temperature. This solution was stirred at 80° C. for 5 hours. It was concentrated under reduced pressure while being azeotropically distilled with xylene and this procedure was repeated three times to obtain the title compound.

PREPARATION EXAMPLE 4

6-(2-Nitroethyl)-2,3-dihydro-1,4-benzodioxine-2-(R)-carboxylic acid ethyl ester

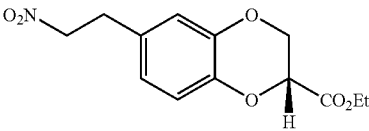

To a solution of 6-(2-nitrovinyl)-2,3-dihydro-1,4-benzodioxine-2-carboxylic acid ethyl ester (3.7 mmol) in dioxane (10 mL) and ethanol (10 mL) was added dropwise a suspension of NaBH$_4$ (140 mg) in dioxane (4 mL) and ethanol (4 mL) under cooling to −10° C. This solution was stirred at −5° C. for 1 hour and then acetic acid was added. It was concentrated under reduced pressure. To the residue were added water and a 1N aqueous solution of sodium hydroxide, and the mixture was extracted with ethyl acetate. The oily phase was washed with saturated aqueous ammonia and brine in turn, dried over anhydrous magnesium sulfate and then concentrated under reduced pressure. The residue was purified by column chromatography on silica gel and the title compound (790 mg) was obtained from the effluent with hexane/ethyl acetate=30/10 (v/v).

¹H-NMR (CDCl₃) δ: 1.23–1.32 (m, 3H), 3.22 (t, 2H, J=7.2 Hz), 4.23–4.32 (m, 2H), 4.35–4.41 (m, 2H), 4.56 (t, 2H, J=7.2 Hz), 4.81 (dd, 1H, J=3.6 Hz, 4.4 Hz), 6.70–6.75 (m, 2H), 6.93–6.98 (m, 1H).

PREPARATION EXAMPLE 5

2-(4-Benzyloxy-2-methoxyphenoxymethyl)-(S)-oxirane

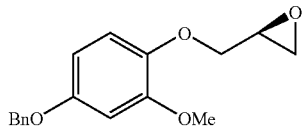

The title compound was prepared using 4-benzyloxy-2-methoxyphenol in the same manner as in Preparation Example 1. Yield: 81%

¹H-NMR (CDCl₃) δ: 2.72 (dd, 1H, J=2.8 Hz, 4.8 Hz), 2.88 (t, 1H, J=2.8 Hz), 3.33–3.40 (m, 1H), 3.84 (s, 3H), 3.98 (dd, 1H, J=5.2 Hz, 11.6 Hz), 4.18 (dd, 1H, J=4.4 Hz, 11.6 Hz), 5.01 (s, 2H), 6.45 (dd, 1H, J=3.2 Hz, 8.8 Hz), 6.59 (d, 1H, J=3.2 Hz), 6.87 (d, 1H, J=8.8 Hz), 7.29–7.46 (m, 5H).

PREPARATION EXAMPLE 6

2-[2-Chloro-4-(methoxymethoxy)phenoxymethyl]-(S)-oxirane

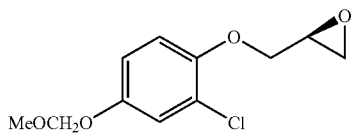

The title compound was prepared using 4-chloro-4-(methoxymethoxy)phenol in the same manner as in Preparation Example 1. Yield: 81%

¹H-NMR (CDCl₃) δ: 2.79 (dd, 1H, J=2.8 Hz, 4.0 Hz), 2.90 (t, 1H, J=4.8 Hz), 3.34–3.40 (m, 1H), 3.47 (s, 3H), 4.00 (dd, 1H, J=5.6 Hz, 11.2 Hz), 4.24 (dd, 1H, J=3.2 Hz, 11.2 Hz), 5.10 (s, 2H), 6.86–6.93 (m, 2H), 7.11 (d, 1H, J=2.4 Hz).

PREPARATION EXAMPLE 7

2-[3-Chloro-4-(methoxymethoxy)phenoxymethyl]-(S)-oxirane

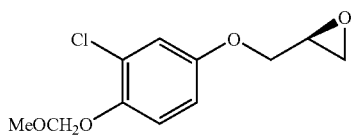

The title compound was prepared using 3-chloro-4-(methoxymethoxy)phenol in the same manner as in Preparation Example 1. Yield: 81%

¹H-NMR (CDCl₃) δ: 2.74 (dd, 1H, J=2.8 Hz, 4.8 Hz), 2.90 (t, 1H, J=4.8 Hz), 3.30–3.36 (m, 1H), 3.53 (s, 3H), 3.89 (dd, 1H, J=5.6 Hz, 7.2 Hz), 4.19 (dd, 1H, J=2.8 Hz, 7.2 Hz), 5.16 (s, 2H), 6.78 (dd, 1H, J=2.8 Hz, 8.8 Hz), 6.97 (d, 1H, J=2.8 Hz), 7.10 (d, 1H, J=8.8 Hz).

PREPARATION EXAMPLE 8

2-(3-Methoxy-4-methoxymethoxy-5-nitrophenoxymethyl)-(S)-oxirane

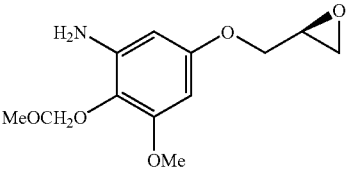

The title compound was obtained using 3-methoxy-4-(methoxymethoxy)phenol in the same manner as in Preparation Example 1. Yield: 73%

¹H-NMR (CDCl₃) δ: 2.76 (dd, 1H, J=2.8 Hz, 4.8 Hz), 2.93 (t, 1H, J=4.8 Hz), 3.31–3.38 (m, 1H), 3.53 (s, 3H), 3.83–3.92 (m, 4H), 4.30 (dd, 1H, J=2.8 Hz, 10.8 Hz), 5.09 (s, 2H), 6.75 (d, 1H, J=2.8 Hz), 6.83 (d, 1H, J=2.8 Hz).

PREPARATION EXAMPLE 9

N-[3-Methoxy-2-methoxymethoxy-5-(S)-oxiranylmethoxyphenyl]-methanesulfonamide

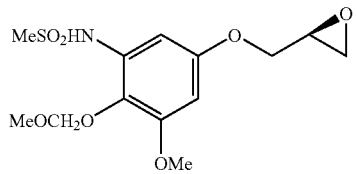

To a solution of 2-(3-methoy-4-methoxymethoxy-5-nitrophenoxymethyl)-(S)-oxirane (270 mg) in ethanol (15 mL) and ethyl acetate (5 mL) was added platinum oxide (27 mg) at room temperature. This solution was stirred at room temperature under hydrogen atmosphere for 3 hours. The solution was filtered through Celite and the filtrate was concentrated under reduced pressure. To a solution of the residue in pyridine (5 mL) was added methanesulfonyl chloride (0.11 mL) under ice cooling. This solution was stirred under ice cooling for 4 hours and ethyl acetate was added thereto. The solution was washed with 3N—HCl, saturated aqueous sodium hydrogecarbonate, water and brine in turn, dried over anhydrous magnesium sulfate and then concentrated under reduced pressure. The residue was purified by column chromatography on silica gel and the title compound (160 mg) was obtained from the effluent with hexane/ethyl acetate=50/50 (v/v). Yield: 66%

¹H-NMR (CDCl₃) δ: 2.76 (dd, 1H, J=2.4 Hz, 4.8 Hz), 2.91 (t, 1H, J=4.8 Hz), 2.98 (s, 3H), 3.31–3.37 (m, 1H), 3.54 (s, 3H), 3.83 (s, 3H), 3.88 (dd, 1H, J=6.4 Hz, 11.2 Hz), 4.27

(dd, 1H, J=2.8 Hz, 11.2 Hz), 5.02 (s, 2H), 6.39 (d, 1H, J=2.8 Hz), 6.76 (d, 1H, J=2.8 Hz), 7.33 (brs, 1H).

PREPARATION EXAMPLE 10

2,6-Dichloro-4-(S)-oxiranylmethoxyphenylamine

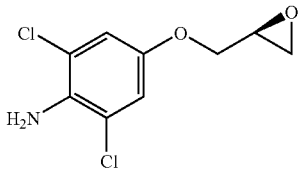

The title compound was prepared using 4-amino-3,5-dichloro-phenol in the same manner as in Preparation Example 1. Yield: 77%

$^1$H-NMR (CDCl$_3$) δ: 2.72 (dd, 1H, J=2.4 Hz, 4.8 Hz), 2.89 (t, 1H, J=4.8 Hz), 3.27–3.34 (m, 1H), 3.83 (dd, 1H, J=5.6 Hz, 11.2 Hz), 4.08–4.20 (m, 3H), 6.85 (s, 2H).

PREPARATION EXAMPLE 11

3-Chloro-5-(S)-oxiranylmethoxypyridine

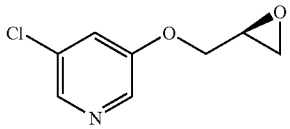

The title compound was prepared using 3-chloro-5-hydroxy-pyridine in the same manner as in Preparation Example 1. Yield: 36%

$^1$H-NMR (CDCl$_3$) δ: 2.77 (dd, 1H, J=2.4 Hz, 4.9 Hz), 2.94 (t, 1H, J=4.4 Hz), 3.33–3.40 (m, 1H), 3.96 (dd, 1H, J=6.1 Hz, 11.0 Hz), 4.33 (dd, 1H, J=2.7 Hz, 11.0 Hz), 7.25–7.27 (m, 1H), 8.22 (d, 1H, J=2.0 Hz), 8.23 (d, 1H, J=2.4 Hz).

PREPARATION EXAMPLE 12

5-(S)-Oxiranylmethoxy-1H-indole

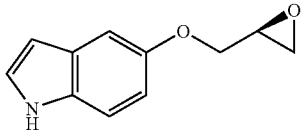

The title compound was prepared using 5-hydroxyindole in the same manner as in Preparation Example 1. Yield: 72%

$^1$H-NMR (CDCl$_3$) δ: 2.78 (dd, 1H, J=2.9 Hz, 4.9 Hz), 2.91 (t, 1H, J=4.4 Hz), 3.37–3.43 (m, 1H), 4.03 (dd, 1H, J=5.6 Hz, 11.0 Hz), 4.24 (dd, 1H, J=3.2 Hz, 11.0 Hz), 6.46–6.49 (m, 1H), 6.90 (dd, 1H, J=2.4 Hz, 8.8 Hz), 7.12 (d, 1H, J=2.0 Hz), 7.19 (t, 1H, J=2.7 Hz), 7.29 (d, 1H, J=8.8 Hz), 8.07 (brs, 1H).

PREPARATION EXAMPLE 13

4-(S)-Oxirannylmethoxy-1H-indole

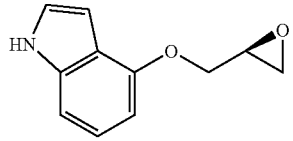

The title compound was prepared using 4-hydroxyindole in the same manner as in Preparation Example 1. Yield: 61%

$^1$H-NMR (CDCl$_3$) δ: 2.81 (dd, 1H, J=2.7 Hz, 5.4 Hz), 2.93 (t, 1H, J=4.4 Hz), 3.43–3.47 (m, 1H), 4.14 (dd, 1H, J=5.4 Hz, 11.0 Hz), 4.35 (dd, 1H, J=3.4 Hz, 11.0 Hz), 6.52 (d, 1H, J=7.8 Hz), 6.68 (dt, 1H, J=1.0 Hz, 2.7 Hz), 7.03 (d, 1H, J=8.3 Hz), 7.08 (d, 1H, J=7.3 Hz), 7.10 (t, 1H, J=2.7 Hz), 8.18 (brs, 1H).

Effect of the Compounds of the Invention

Representative compounds of the invention were assayed for their stimulating activity of human β3 adrenergic receptor. In the tests, there was used G4-I cloned with CHO cells expressing human β3 adrenergic receptor genes. A cAMP EIA kit for use was available from Amersham Farmacia.

[Test Methods]

G4-I was incubated under the atmosphere of 5% CO$_2$ at 37° C. in a Han's F12 Nutrient Mixture medium containing 10% fetal calf serum, penicillin 100 U/mL, streptomycin 100 μg/mL, amphotericin B 25 μg/mL and Geneticin 400 μg/mL. When the reaction for cAMP production was carried out, frozen cells stocked were incubated for 3 days and then treated with trypsin to prepare a cell suspension. The cell suspension was diluted to 2×10$^5$ cells/mL with the medium. Then 1 ml each of the diluted suspension was dispensed into a 12-well plate dish.

The cells cultured for 24 hours were used to carry out the cAMP production reaction.

(1) Buffers Used

The composition of each buffer for use is shown below.

Wash Buffer

Composition: 1×Hank's Balanced Solution containing 20 mM Hepes-NaOH (pH 7.4)

Reaction Buffer

Composition: 1×Hank's Balanced Solution containing 1 mM ascorbic acid, 0.25 mM 3-isobutyl-1-methyl-xanthine and 20 mM Hepes-NaOH (pH 7.4)

Extraction Buffer

Composition: 5 mM Tris-HCl, 2 mM EDTA (pH 7.4)

(2) Reaction for cAMP Production

The culture medium was removed from the cells incubated on the 12-well plate dish. The cells were washed twice with 1 mL of Wash Buffer previously warmed to 37° C. and then 0.9 mL of Reaction Buffer was added. Cultivation was carried out on a water bath at 37° C. for 5 minutes and then 0.1 mL of an aqueous solution of the test compound or isoproterenol was added thereto. Reaction was further allowed to take place at 37° C. for 30 minutes. The reaction solution was taken out and then washed twice with 2 mL of D-PBS(-) followed by addition of 1 mL of the Extraction Buffer. The extraction procedure was performed using a plate mixer at 4° C. for 1 hour. The extract was stored at −20° C.

(3) cAMP Assay

The cell extract frozen at −20° C. was thawed at 4° C. The cAMP of the extract in each well was assayed by means of a cAMP-EIA kit manufactured by Amersham Farmacia. Assay was performed in accordance with the manual attached to the kit. Adsorbance in a 96-well plate was determined using a microplate reader (Model Spectra MAX 250) manufactured by Molecular Device.

(4) Determination of Cell Protein Amount

The protein amount of the above cell extract was assayed according to the dye-binding method using a CBB solution for quantitative determination of protein (available from Bio-Rad). Bovine serum albumin was used as a protein standard, and absorbance was determined using the above microplate reader (Model Spectra MAX 250) manufactured by Molecular Device.

(5) Data Processing

Determination of cAMP and protein amounts was carried out in duplicate and mean values were adopted as measured values. The cAMP production amount of each sample was represented in terms of a numerical value of the cAMP amount (pmol) divided by cell protein amount (mg) (pmol/mg protein). Each test was carried out in duplicate (using 2 wells) under the respective conditions, and a mean value from the duplicate tests was adopted as the test result. For each sample, cAMP production amount was calculated and a relative cAMP production amount to the maximum cAMP production amount of isoproterenol (% of isoproterenol Max) was determined.

TABLE 1

| Test compound | Concentration (μM) | Intrinsic Activity (% of ISP) |
|---|---|---|
| Example 2 | 1 | 76 |
| Example 4 | 1 | 98 |
| Example 12 | 10 | 73 |
| Example 16 | 1 | 61 |

As is apparent from Table 1, the compounds of this invention have intrinsic activity to human β3 adrenergic receptor, which is not at the level of a conventional partial agonist, but which is nearly at the level of a full agonist and is also higher than that of the compound described in FR2746395. Thus it is concluded that they are a highly excellent stimulating agent for human β3 adrenergic receptor.

The compounds of the general formula (I) according to this invention may be administered in various forms. The dosage forms may include, for example, oral administration forms such as tablets, capsules, granules, powders, and syrups, or parental administration forms such as injections (intravenously, intramuscularly, subcutaneously), drips, and suppositories. These various preparations may be formulated using active ingredients and known auxiliaries that can be used in the field of pharmaceutical preparations, such as excipients, binding agents, disintegrating agents, lubricants, correctives, solubilizing agents, suspending agents, coating agents, etc., according to a conventional method. The dose varies depending on the severity of diseases, the age and body weight of patients and administration routes, but it may be usually administered to an adult in an amount of 0.01 mg to 2000 mg per day.

Specific examples of pharmaceutical preparations containing the compound of this invention as an active ingredient will be illustrated by way of pharmaceutical preparation examples described below.

| Pharmaceutical Preparation Example 1 Tablet (one tablet) | |
|---|---|
| Compound of Example 4 | 0.5 mg |
| Lactose | 70 mg |
| Crystalline cellulose | 20 mg |
| Corn starch | 8 mg |
| Magnesium stearate | 1 mg |
| Total amount | 100 mg |

All ingredients were uniformly mixed to form powders for direct compression. The powders were made into tablets in a rotary tableting machine, each tablet having a diameter of 6 mm and a weight of 100 mg.

| Pharmaceutical Preparation Example 2 Granule (per divided packet) | | |
|---|---|---|
| A | Compound of Example 12 | 0.5 mg |
|   | Lactose | 90 mg |
|   | Crystalline cellulose | 50 mg |
|   | Corn starch | 50 mg |
| B | Hydroxypropylcellulose | 10 mg |
|   | Ethanol | 10 mg |

After all ingredients of the above group A were uniformly mixed, a solution of the above group B was added thereto and kneaded. The mixture was granulated by the extrusion granulation method, and then dried in a drier at 50° C. The dried granules were sieved to granules between 297 μm and 1460 μm sizes, to give granules weighing 200 mg per divided packet.

| Pharmaceutical Preparation Example 3 Syrup | |
|---|---|
| Compound of Example 35 | 0.050 g |
| Sucrose | 30.000 g |
| D-sorbitol, 70 W/V % | 25.950 g |
| Ethyl paraoxybenzoate | 0.015 g |
| Propyl paraoxybenzoate | 0.015 g |
| Flavor | 0.200 g |
| Glycerol | 0.150 g |
| 96% Ethanol | 0.500 g |
| Distilled water | q. s. to make up a total volume of 100 mL |

Sucrose, D-sorbitol, ethyl paraoxybenzoate, propyl paraoxybenzoate and the compound of Example 35 were dissolved in 60 g of warm water. After cooling, glycerol and a solution of flavor dissolved in ethanol were added. Then, distilled water was added to the mixture to make up a total volume of 100 mL.

Industrial Applicability

The propanolamine derivatives having a 1,4-benzodioxane ring of this invention are useful as prophylactic or therapeutic agents for diabetes, obesity, hyperlipemia, depression, a respiratory disease, or a gastrointestinal disease in a mammal.

The invention claimed is:

1. A 2-(S)-hydroxy-3-substituted propanolamine derivative having a 6-substituted 2,3-dihydro-1,4-benzodioxine ring wherein the 2-position is substituted with a carboxy group or a ($C_1$–$C_6$)alkoxycarbonyl group and is provided with R configuration, represented by formula (II):

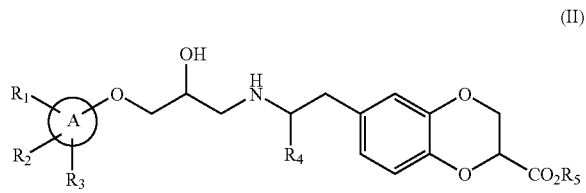

wherein $R_1$ is a ($C_1$–$C_6$)alkylsulfonamido group; and $R_2$ and $R_3$ may be the same or different and each represents a hydrogen atom, a ($C_1$–$C_6$)alkoxy group, a ($C_1$–$C_6$)alkoxy ($C_1$–$C_6$)alkoxy group, a hydroxy group, a ($C_1$–$C_6$)alkylsulfonamido group or an amino group,
$R_4$ represents a hydrogen atom or a ($C_1$–$C_6$)alkyl group,
$R_5$ represents a hydrogen atom or a ($C_1$–$C_6$)alkyl group, and
A represents a benzene ring, or a pharmacologically acceptable salt thereof.

2. The compound as claimed in claim 1, wherein the compound is selected from the following compounds:
6-[2-(R)-[2-(S)-hydroxy-3-(4-hydroxy-3-methanesulfonamido-phenoxy)propylamino]propyl]-2,3-dihydro-1,4-benzodioxine-2-(R)-carboxylic acid,
6-[2-[2-(S)-hydroxy-3-(4-hydroxy-3-methanesulfonamido-phenoxy]propylamino]ethyl]-2,3-dihydro-1,4-benzodioxine-2-(R)-carboxylic acid,
6-[2-(R)-[2-(S)-hydroxy-3-[3-methanesulfonamido-4-(methoxymethoxy)phenoxy]propylamino]propyl]-2,3-dihydro-1,4-benzodioxine-2-(R)-carboxylic acid ethyl ester,
6-[2-[2-(S)-hydroxy-3-[3-methanesulfonamido-4-(methoxymethoxy)phenoxy]propylamino]ethyl]-2,3-dihydro-1,4-benzodioxine-2-(R)-carboxylic acid ethyl ester,
6-[2-(R)-[2-(S)-hydroxy-3-(4-hydroxy-3-methanesulfonamido-5-methoxyphenoxy)propylamino]propyl]-2,3-dihydro-1,4-benzodioxine-2-(R)-carboxylic acid ethyl ester, and
6-[2-(R)-[2-(S)-hydroxy-3-[3-methanesulfonamido-5-methoxy-4-(methoxymethoxy)phenoxy]propylamino]propyl]-2,3-dihydro-1,4-benzodioxine-2-(R)-carboxylic acid ethyl ester.

3. A pharmaceutical composition which comprises a compound as claimed in any of claims 1, 2 or 6 or a pharmacologically acceptable salt thereof as an active ingredient and, if necessary, pharmaceutically acceptable auxiliaries.

4. A therapeutic agent for diabetes, obesity or hyperlipemia in a mammal which comprises a compound as claimed in any of claims 1, 2 or 6 or a pharmacologically acceptable salt thereof as an active ingredient.

5. A method of treating diabetes, obesity or hyperlipemia in a mammal in need of such treatment or prevention, which comprises administering to the mammal, an effective amount of a compound as claimed in any of claims 1, 2 or 6 or a pharmacologically acceptable salt thereof.

6. A compound selected from the following compounds:
6-[2-(R)-[2-(S)-hydroxy-3-(4-hydroxy-2-methoxyphenoxy)-propylamino]propyl]-2,3-dihydro-1,4-benzodioxine-2-(R)-carboxylic acid,
6-[2-[2-(S)-hydroxy-3-(4-hydroxy-2-methoxyphenoxy)propylamino]ethyl]-2,3-dihydro-1,4-benzodioxine-2-(R)-carboxylic acid, and
6-[2-[2-(S)-hydroxy-3-(4-hydroxy-2-methoxyphenoxy)-propylamino]ethyl]-2,3-dihydro-1,4-benzodioxine-2-(R)-carboxylic acid ethyl ester.

* * * * *